(12) United States Patent
Bell et al.

(10) Patent No.: US 7,662,996 B2
(45) Date of Patent: Feb. 16, 2010

(54) GENERATION OF ENDO- AND/OR EXO-NORBORNENECARBOXALDEHYDE AS AN INTERMEDIATE TO FUNCTIONALIZED NORBORNENES

(75) Inventors: Andrew Bell, Lakewood, OH (US); Brian Knapp, Medina, OH (US); Dane Jablonski, Brunswick, OH (US); Dietrich Fabricius, Hendersonville, NC (US); Peter Wyatt Newsome, Horse Shoe, NC (US)

(73) Assignee: Promerus, LLC, Brecksville, OH (US)

( * ) Notice: Subject to any disclaimer, the term of this patent is extended or adjusted under 35 U.S.C. 154(b) by 0 days.

(21) Appl. No.: 12/262,924

(22) Filed: Oct. 31, 2008

(65) Prior Publication Data

US 2009/0118539 A1 May 7, 2009

Related U.S. Application Data

(60) Provisional application No. 60/985,393, filed on Nov. 5, 2007.

(51) Int. Cl.
*C07C 61/28* (2006.01)
*C07C 35/00* (2006.01)

(52) U.S. Cl. ........................... 562/502; 568/820

(58) Field of Classification Search .................. None
See application file for complete search history.

(56) References Cited

OTHER PUBLICATIONS

Blanco et al, Tetrahedron, Divergent Synthesis of Two Precursors of 3'-Homo-2'-deoxy- and 2'-Homo-3'-deoxy-Carboxylic Nucleosides, 2002, 58, pp. 8843-8849) in view of Perrier et al (Centre National de Recerche Scientifique, Paris, 1977 1(5), pp. 367-368.*
Perrier et al, Centre National de Recerche Scientifique, Paris, 1977 1(5), pp. 367-368.*
Belikova et al, Zhurnal Obshchei Kimii, Synthesis of Endo- and Exo-2-methylbicyclo[2.2.1]heptanes. Steric Orientation of the Reaction of Cyclopentadiene With Propylene, 1962, 32, pp. 2942-2951, English abstract only.*
International Search Report for International Application No. PCT/US 08/82339 dated Jan. 22, 2009.
Written Opinion of the International Searching Authority for International Application No. PCT/US 08/82339 mailed on Jan. 22, 2009.

* cited by examiner

*Primary Examiner*—Paul A Zucker
(74) *Attorney, Agent, or Firm*—Turocy & Watson, LLP

(57) ABSTRACT

Embodiments in accordance with the present invention provide for forming essentially pure diastereomers of 5/6-substituted norbornene-type monomers. Further, embodiments in accordance with the present invention encompass polymerizing such diastereomers to form addition or ROMP polymers where a desired exo-/endo-ratio of the diastereomers is provided to the polymerization, such ratio designed to provide a desired ratio of endo-/exo-structured repeating units for a resulting polymer to have desired physical or chemical properties.

20 Claims, 1 Drawing Sheet

GENERATION OF ENDO- AND/OR EXO-NORBORNENECARBOXALDEHYDE AS AN INTERMEDIATE TO FUNCTIONALIZED NORBORNENES

CROSS-REFERENCE TO RELATED APPLICATIONS

This application claims the benefit of priority to U.S. Provisional Application Ser. No. 60/985,393 filed Nov. 5, 2007, the entire contents of which are hereby incorporated by reference.

TECHNICAL FIELD

The present invention relates generally to the preparation of functionalized exo- and/or endo-norbornene-type monomers and more specifically to methods for the preparation of endo- and/or exo-norbornenecarboxaldehyde and of the aforementioned functionalized monomers therefore.

DETAILED DESCRIPTION

Figure 1:
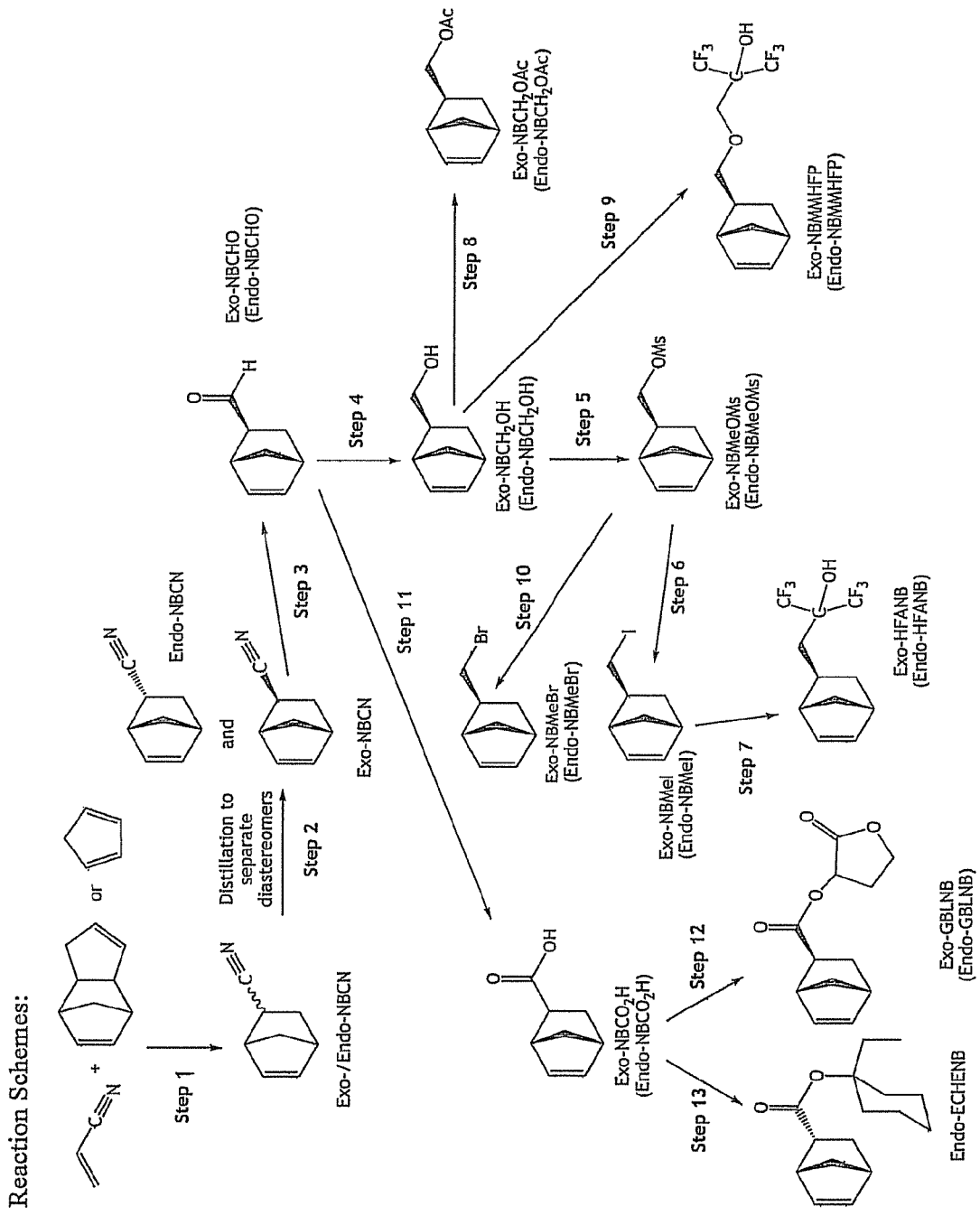
FIG. 1 depicts various reactions schemes in accordance with embodiments of the invention.

The reactivity of 4/5 substituted norbornene (NB) monomers employed in addition polymerization (AP) and ring-opening metathesis polymerization (ROMP) has been found to depend, in part, on the relative concentration of the exo monomer in the monomer starting material and the spacing of the functional group (FG) portion of the 4/5 substituent from the monomer's bicyclic structure portion. While synthetic routes to generate diastereomerically pure endo- and/or exo-functionally substituted norbornene monomers (NBFG) are known, none are routine methods that begin from a generally available feedstock. Therefore it would advantageous to have one or more such routine, cost effective methods for the forming of such diastereomerically pure endo- and/or exo-NBFG monomers.

Exemplary embodiments in accordance with the present invention will be described herein below. Various modifications, adaptations or variations of such exemplary embodiments may become apparent to those skilled in the art as such embodiments are disclosed. It will be understood that all such modifications, adaptations or variations that rely upon the teachings of the present invention, and through which these teachings have advanced the art, are considered to be within the scope and spirit of the present invention.

For example, while the examples provided herein are presented to demonstrate some embodiments in accordance with the present invention that make use of essentially pure exo- and endo-norbornenecarboxaldehyde (NBCA) to create norbornene monomers having other function groups, such examples are not exhaustive of all possible reactions that can make use of a NBCA intermediate. However, such other reactions, being generally known, are believed to be within the scope and spirit of the present invention.

Other than in the operating examples, or where otherwise indicated, all numbers, values and/or expressions referring to quantities of ingredients, reaction conditions, etc., used in the specification and claims are to be understood as modified in all instances by the term "about."

Various numerical ranges are disclosed in this patent application. Because these ranges are continuous, unless specifically noted otherwise, they include the minimum and maximum values of each range and every value therebetween. Furthermore, unless expressly indicated otherwise, the various numerical ranges specified in this specification and in the claims are approximations that are reflective of the various uncertainties of measurement encountered in obtaining such values.

As used herein, "hydrocarbyl" refers to a radical of a group that contains only carbon and hydrogen, non-limiting examples being alkyl, cycloalkyl, aryl, aralkyl, alkaryl, and alkenyl. The term "halohydrocarbyl" refers to a hydrocarbyl group where at least one hydrogen has been replaced by a halogen. The term "perhalocarbyl" refers to a hydrocarbyl group where all hydrogens have been replaced by halogens. In addition, in some embodiments in accordance with the present invention, the terms hydrocarbyl, halohydrocarbyl or perhalocarbyl can encompasses one or more heteroatoms such as O, N, S and Si. Exemplary groups encompassing heteroatoms include, among others, a maleimide group, a triethoxysilyl group, a trimethoxysilyl group, a methyl acetate group, a hexafluoroisopropyl alcohol group, a trifluoromethanesulfonamide group and a t-butylcarboxylate group.

As used herein, "alkyl" refers to a linear or branched acyclic or cyclic, saturated hydrocarbon group having a carbon chain length of, for example, from $C_1$ to $C_{25}$. Nonlimiting examples of suitable alkyl groups include, but are not limited to, $-CH_3$, $-(CH_2)_2CH_3$, $-(CH_2)_4CH_3$, $-(CH_2)_5CH_3$, $-(CH_2)_{10}CH_3$, $-(CH_2)_{23}CH_3$.

As used herein the term "aryl" refers to aromatic groups that include, without limitation, groups such as phenyl, biphenyl, benzyl, tolyl, dimethylphenyl, xylyl, naphthalenyl, anthracenyl and the like, as well as heterocyclic aromatic groups that include, without limitation, pyridinyl, pyrrolyl, furanyl, thiophenyl and the like.

As used herein, "alkenyl" refers to a linear or branched acyclic or cyclic hydrocarbon group having one or more double bonds and having an alkenyl carbon chain length of $C_2$ to $C_{25}$.

As used herein the terms "alkaryl" or "aralkyl" refer to a linear or branched acyclic alkyl group substituted with at least one aryl group, for example, phenyl, and having an alkyl carbon chain length of $C_2$ to $C_{25}$.

Any of the aforementioned groups can be further substituted, if desired. Such substituents can include a functional group (FG) or moiety such as hydroxyl groups, carboxylic acid and carboxylic acid ester groups. Also, such groups as a halogen other than fluorine (Cl, Br, I), a nitrile (C≡N), amine ($NR_2$ where each R is independently hydrogen or hydrocarbyl), tosylate ($-SO_2-C_6H_5-CH_3$, Ts) mesylate ($-SO_2-CH_3$, Ms), acid chloride ($-C(O)-Cl$), or amide ($-C(O)-NR_2$, where at least one R is hydrogen) and the like are also advantageous substituents for the aforementioned groups.

As used herein reference to norbornene carboxylic acid derivatives include, but are not limited to, esters, amides, imines, acid halides and the like. In addition, reference herein to norbornene alcohol derivatives include, but are not limited to, ethers, epoxides, protected alcohols such as esters, and like. Still further, reference above to substituted hydrocarbyls is also inclusive of the carboxylic acids, and derivatives, and the alcohols, and derivatives, defined above. Thus, as used herein, the term "functional group" of "FG" will be understood to mean a substituent other than a hydrocarbyl.

As used herein, the term "essentially pure," "pure," or "high purity" when referring to, for example a monomer, a polymer or diastereomer of some embodiments of the present invention, means that the purity of such material is at least 95%. In other embodiments such terms mean that the purity of such materials is at least 98%, and in still other embodiments such terms mean that the purity of such materials is 99% or greater.

As used herein, the term "transition metal polymerizations" is used as a generic term to mean either addition polymerization (AP) or ring opening metathesis polymerization (ROMP).

For some embodiments in accordance with the present invention, it has been found that employing either an essentially pure exo-monomer or an essentially pure endo-monomer as feedstock for addition polymerization provides several advantages over using diastereomeric mixtures of such monomers. For example, as compared to diastereomeric mixtures, the addition polymerization of essentially pure exo-monomers result in (i) improved monomer to polymer conversion, (ii) reduced polymerization times, (iii) lower catalyst loadings and (iv) enhanced control of polymer homogeneity. Where either essentially pure endo- or exo-monomers are employed as feedstock for addition polymerization enhanced control of polymer homogeneity is also observed. Additionally, the polymerization of single diastereomers can facilitate the tailoring of some polymer properties. For example, generally a property such as the dissolution rate of a polymer formed from an essentially pure exo diastereomer is different from such rate for a polymer formed from the analogous essentially pure endo diastereomer, thus where a specific dissolution rate is desired, embodiments in accordance with the present invention allow the mixing of appropriate amounts of each isomer to obtain a specific dissolution rate.

Therefore it should be appreciated that in some transition metal polymerizations, it can be advantageous to perform such polymerizations using monomer feedstock that is an essentially pure diastereomer, while in other polymerizations a mixture of the diastereomers having a specific ratio might be desirable. It should also be realized that although an all exo-NB monomer feedstock will generally give the highest reactivity, and an all endo-NB monomer feedstock will generally give the lowest reactivity, in systems where a copolymer is being formed from functionally different norbornene-type monomers the relative reaction rates of such different monomers may require the matching of an endo to exo isomer ratio in the feedstock to maintain the appropriate reactivity control and achieve the desired isomer ratio in the polymer being formed. It follows then that it is advantageous to have the ability to formulate any desired exo/endo monomer reactant ratio for the transition metal polymerization of such monomers, and maintain this reactant ratio through either a continuous or semi-batch metering strategy.

Some embodiments of in accordance with the present invention are therefore directed to methods for forming essentially pure exo- and/or endo-NB monomers in accordance with Formula I:

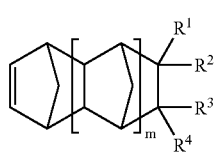

Formula I where m is an integer from 0 to 3 and each occurrence of $R^1$, $R^2$, $R^3$ and $R^4$ independently represents hydrogen, a hydrocarbyl or a functional group (FG) substituent.

When any of $R^1$ to $R^4$ is a hydrocarbyl group, such group can be a $C_1$ to $C_{30}$ alkyl, aryl, aralkyl, alkaryl, alkenyl, alkynyl, cycloalkyl, cycloalkenyl, alkylidenyl or alkylsilyl group. Representative alkyl groups include, but are not limited to, methyl, ethyl, propyl, isopropyl, butyl, isobutyl, sec-butyl, tert-butyl, pentyl, neopentyl, hexyl, heptyl, octyl, nonyl, decyl and dodecyl. Representative alkenyl groups include, but are not limited to, vinyl, allyl, butenyl and cyclohexenyl. Representative alkynyl groups include, but are not limited to, ethynyl, 1-propynyl, 2-propynyl, 1-butynyl and 2-butynyl. Representative cycloalkyl groups include, but are not limited to, cyclopentyl, cyclohexyl and cyclooctyl substituents. Representative aryl groups include, but are not limited to, phenyl, tolyl, dimethylphenyl, naphthyl and anthracenyl. Representative aralkyl groups include, but are not limited to, benzyl and phenethyl. Representative alkylidenyl groups include, but are not limited to, methylidenyl, ethylidenyl, propylidenyl, and isopropylidenyl groups. In addition, it should be noted that the hydrocarbyl groups mentioned above can themselves be substituted, that is to say one of the hydrogen atoms can be replaced, with linear and/or branched $C_1$-$C_{10}$ alkyl, haloalkyl and perhaloalkyl groups, aryl groups and cycloalkyl groups and or include one or more heteroatoms such as O, N, S or Si, among others.

Any of $R^1$ to $R^4$ can also be a halohydrocarbyl group, where such group includes any of the hydrocarbyls mentioned above where at least one, but less than all, of the hydrogen atoms of the hydrocarbyl are replaced by a halogen (fluorine, chlorine, bromine or iodine). Additionally, any of $R^1$ to $R^4$ can be a perhalocarbyl, where such group includes any of the hydrocarbyls mentioned above where all of the hydrogen atoms of the hydrocarbyl are replaced by a halogen. Useful perfluorinated substituents include, but are not limited to, perfluorophenyl, perfluoromethyl, perfluoroethyl, perfluoropropyl, perfluorobutyl and perfluorohexyl.

When the pendant group(s) is a FG substituent, any of $R^1$ to $R^4$ independently represent a linear or branched carboxylic acid, carboxylic acid ester, ether, alcohol and carbonyl groups. Representative examples of such substituents are functional substituents that include, but are not limited to, radicals selected from —$(CR*_2)_n$—$C(O)OR^5$, —$(CR*_2)_n$—$OR^5$, —$(CR*_2)_n$—$C(O)R^5$, —$(CR*_2)_n SiR^5$, —$(CR*_2)_n Si(OR^5)_3$, A—O—[—$(C(R^5)_2)_n$—O—$]_n$—$(C(R^5)_2)_n$—OH and $R^5(Z)$, where each n independently represents an integer from 0 to 10, R* can be hydrogen or halogen and each $R^5$ independently represents hydrogen, a halogen, a $C_1$ to $C_{30}$ alkyl, aryl, aralkyl, alkaryl, alkenyl, alkynyl, cycloalkyl, cycloalkenyl and alkylidenyl group, that can also contain one or more hetero atoms. Further, A is a linking group selected from a $C_1$ to $C_6$ linear, branched, or cyclic alkylene, and Z is a functional group selected from hydroxyl, carboxylic acid, amine, thiol, isocyanate and epoxy. Representative hydrocarbyl groups set forth under the definition of $R^5$ is the same as those identified above under the definition of $R^1$ to $R^4$. Further, $R^5$ can represent a moiety selected from —$C(CH_3)_3$, —$Si(CH_3)_3$, —$CH(R^6)OCH_2CH_3$, —$CH(R^6)OC(CH_3)_3$ or the following cyclic groups:

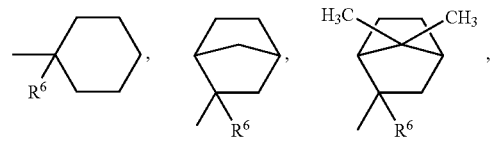

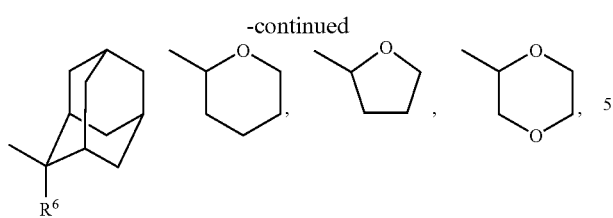

where $R^6$ represents hydrogen or a linear or branched ($C_1$-$C_5$)alkyl group. Such alkyl groups include methyl, ethyl, propyl, i-propyl, butyl, i-butyl, t-butyl, pentyl, t-pentyl and neopentyl. In the above structures, the single bond line projecting from the cyclic groups indicates the position where the cyclic group is bonded to any of the aforementioned $R^5$-containing substituents. Further examples of $R^6$ radicals include 1-methyl-1-cyclohexyl, isobornyl, 2-methyl-2-isobornyl, 2-methyl-2-adamantyl, tetrahydrofuranyl, tetrahydropyranoyl, 3-oxocyclohexanonyl, mevalonic lactonyl, 1-ethoxyethyl and 1-t-butoxy ethyl.

$R^5$ can also represent dicyclopropylmethyl (Dcpm), and dimethylcyclopropylmethyl (Dmcp) groups which are represented by the following structures:

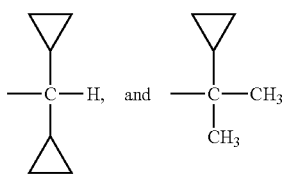

In some embodiments employing monomers in accordance with Formula I, the perhalohydrocarbyl groups can include perhalogenated phenyl and alkyl groups. In other embodiments, the perfluorinated substituents can include perfluorophenyl, perfluoromethyl, perfluoroethyl, perfluoropropyl, perfluorobutyl and perfluorohexyl. In addition to the halogen substituents, cycloalkyl, aryl and aralkyl groups of such embodiments can be further substituted with linear and branched $C_1$-$C_5$ alkyl and haloalkyl groups, aryl groups and cycloalkyl groups. Non-limiting examples of such monomers include structural formulae depicted in Structural Groups MM, NN and PP.

In other embodiments, polycyclic olefin monomers include, but are not limited to, 5-norbornene-2-methanol hydroxyethylether, t-butyl ester of 5-norbornene 2-carboxylic acid, hydroxyethylester of 5-norbornene carboxylic acid, trimethylsilane ester of 5-norbornene carboxylic acid, 5-norbornene-2-methanol acetate, 5-norbornene-2-methanol, 5-norbornene-2-ethanol, 5-triethoxysilylnorbornene, 1-methylcyclopentyl ester of 5-norbornene carboxylic acid, tetrahydro-2-oxo-3-furanyl ester of 5-norbornene carboxylic acid and mixtures thereof.

In still other embodiments, at least one of $R^1$ and $R^4$ of Formula I is a $QNHSO_2R^8$ group or a $Q^{\ddagger}(CO)O—(CH_2)_m—R^8$ group, where Q a linear or branched alkyl spacer of 2 to 5 carbons and $Q^{\ddagger}$ is an optional linear or branched alkyl spacer of 1 to 5 carbons, m is either 0 or an integer from 1 to 3, inclusive, and $R^8$ is a perhalo group of 1 to about 10 carbon atoms. The others of $R^1$ to $R^4$ are each generally hydrogen.

In yet other embodiments, at least one of $R^1$ to $R^4$ is one of groups AA, BB or CC, and the others are each generally hydrogen (please note that each of the representations of functional groups AA through KK and KJH can be either exo- or an endo-substituted):

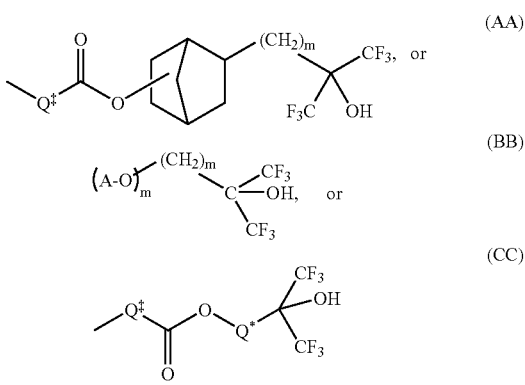

where each m is defined as above and independently selected, $Q^{\ddagger}$ is also as defined above, $Q^*$ is a linear or branched alkyl spacer of 1 to 5 carbons and A is an a linear or branched alkyl spacer of from 1 to 8 carbons. In some embodiments encompassing groups AA or CC, $Q^{\ddagger}$ is not present or is a linear alkyl spacer of 1 to 3 carbons. Additionally, for group CC, $Q^*$ can be a linear or branched spacer of 3 or 4 carbons. In other such embodiments, $Q^{\ddagger}$ is not present or is 1 carbon atom. In other embodiments encompassing group BB, m is either 1 or 2. In exemplary embodiments of the encompassing repeating units represented by Formula I, one of $R^1$ to $R^4$ is group BB while the others are each hydrogen, n is 0 and each m is 1.

In yet other embodiments, at least one of $R^1$ to $R^4$ of Formula I is one of groups DD, EE or FF, and the others are each generally hydrogen:

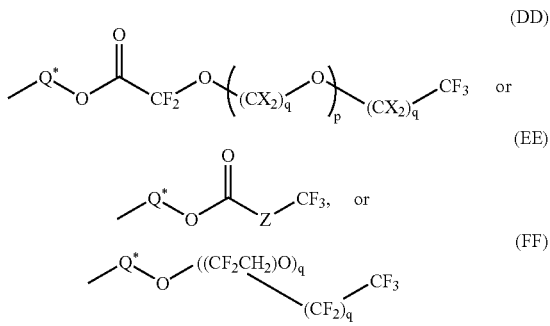

where each X is independently either fluorine or hydrogen, each q is independently an integer from 1 to 3, p is an integer from 1 to 5, $Q^*$ is as defined above, and Z is a linear or branched halo or perhalo spacer of 2 to 10 carbons. In some embodiments encompassing group DD, $Q^*$ is a single carbon spacer, X is fluorine, q is 2 or 3 and p is 2. In some embodiments encompassing group EE, $Q^*$ is a single carbon spacer and Z is a branched fluorinated alkyl chain of up to 9 carbons units. In some embodiments encompassing group FF, $Q^*$ is a single carbon spacer and q is 1 or 2.

In other embodiments, at least one of $R^1$ to $R^4$ is a group represented by the formula GG, and the others are each generally hydrogen:

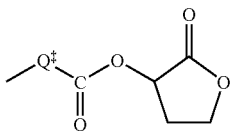

where Q‡, if present, is an optional linear or branched alkyl spacer where of 1 to 5 carbons. In some other embodiments one of R¹ to R⁴ is a group represented by formula GG, each of the others is hydrogen and Q‡ is not present or is a linear alkyl spacer of 1 to 3 carbons.

In other embodiments in accordance with Formula I, at least one of R¹ to R⁴ is a group represented by one of HH, JJ or KK shown below, and the others are each generally hydrogen:

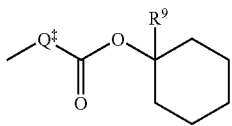

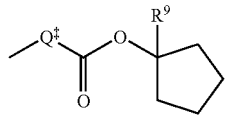

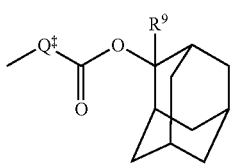

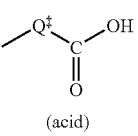

(acid)

where Q‡ is as defined above and R⁹ is a linear or branched alkyl group of 1 to about 5 carbon atoms. It should be noted that the HJK (acid) group represented above, is derived from one of the H, J or K groups.

The monomer compositions employed for embodiments in accordance with the present invention can include any one or multiple variations of the polycyclic olefin monomers of Formula I. Thus, polymers formed by embodiments in accordance with the present invention can encompass homopolymers and polymers that incorporate any monomer that is in accordance with Formula I. Exemplary monomers in accordance with Formula I are depicted in Structural Groups MM, NN and PP shown below, where any of such monomer representations is understood to depict both the exo- and endo-isomer:

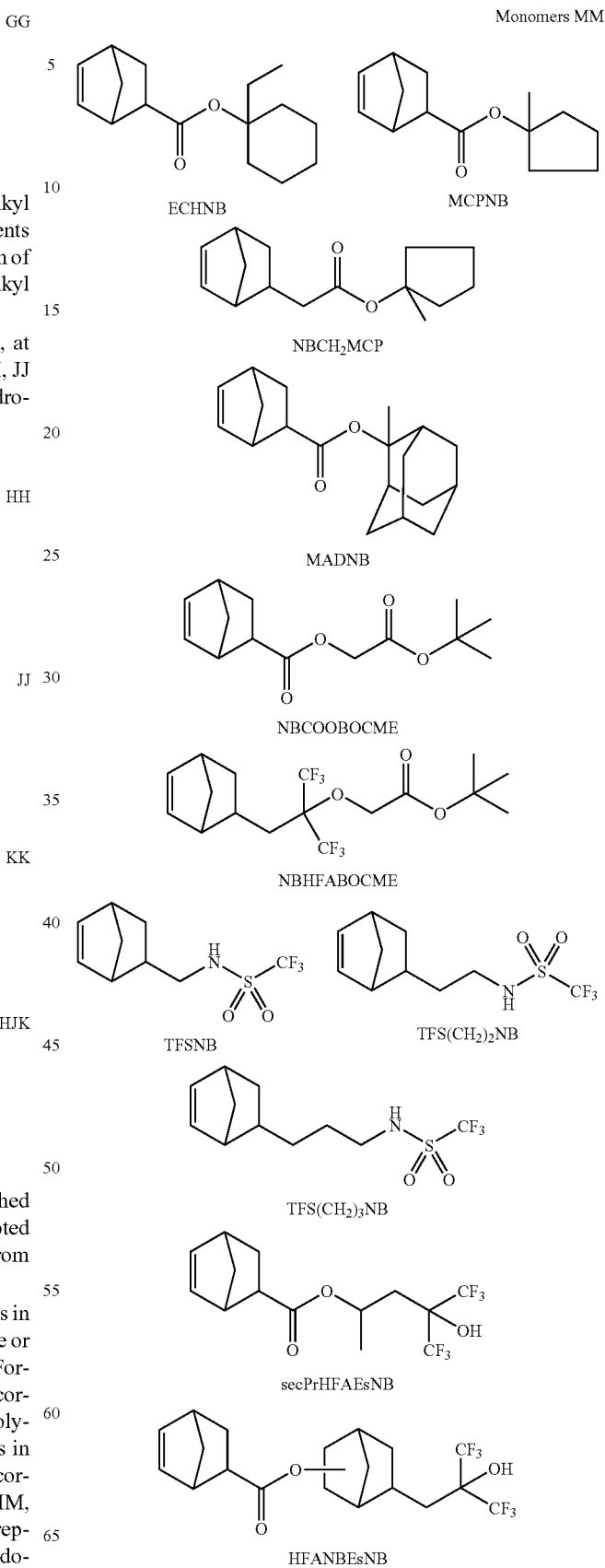

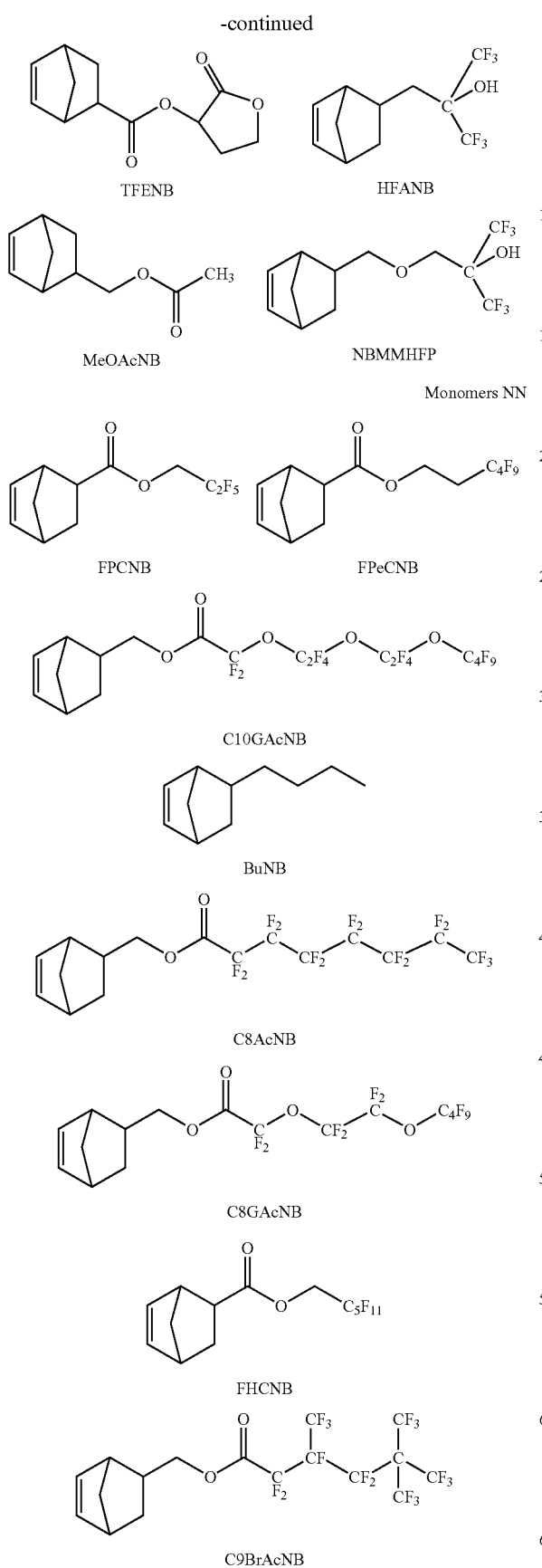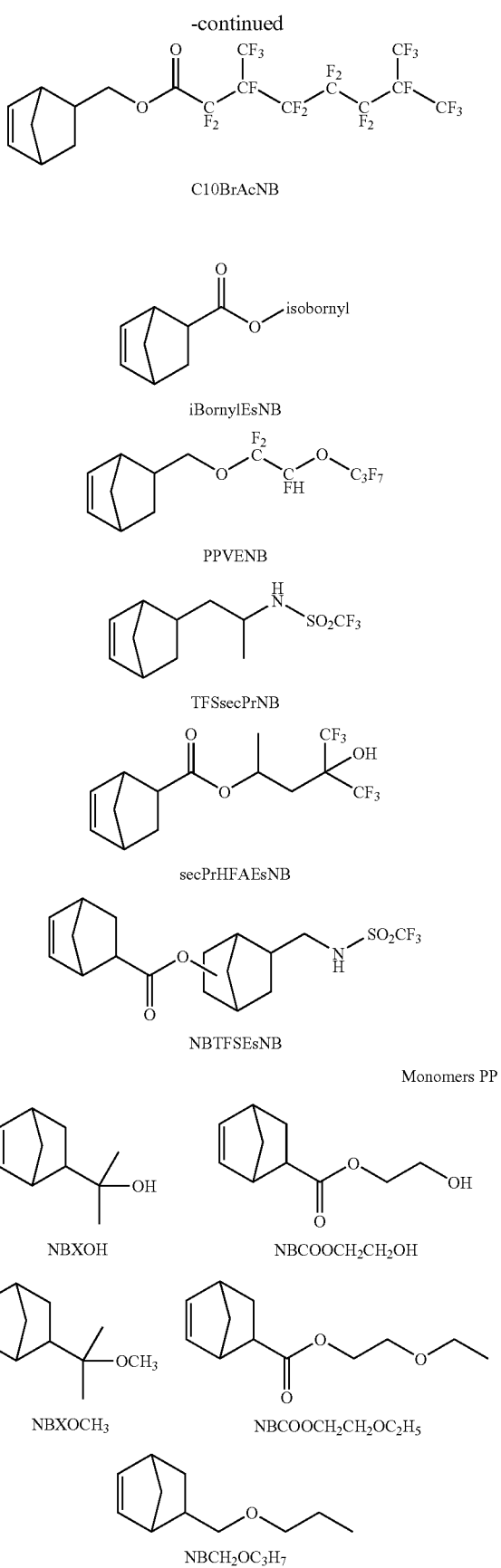

-continued

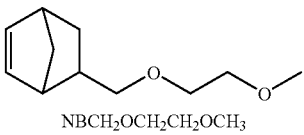

NBCH₂OCH₂CH₂OCH₃

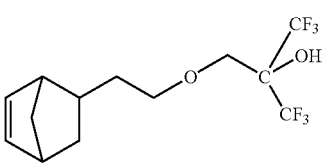

NBEMHFP

As mentioned above, all of the functional groups AA through KK and KJH are inclusive of either an exo- or endo-substituted group as are the substituents shown in Monomers MM, NN or PP and thus are consistent with the generic representations Formula IIa and IIb:

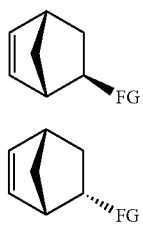 Formula IIa

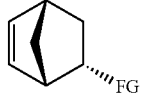 Formula IIb where FG represents a functional group and is one of $R^1$, $R^2$, $R^3$ or $R^4$ of Formula I and m is 0.

For some embodiments in accordance with the present invention, the monomers of Formula IIa and IIb are further subjected to a Diels-Alder reaction with cyclopentadiene (CPD) to generate a CPD homolog, such as tetracyclododecene-type monomers (m of Formula I is 2). In other embodiments m of Formula I can be 3 or larger via a similar reaction with CPD. As one of skill in the should know, the products of such a Diels-Alder reaction is governed by, in pertinent part, the sterics of both the CPD and the NBFG, therefore where the NBFG is a pure exo-monomer, it will yield different compositions of the polycyclic rings than where the NBFG is a pure endo-NBFG monomer, as shown below. In some cases, there is an enhanced reaction and improved yield for the TD molecules when exo-NBFG is employed as a reactant.

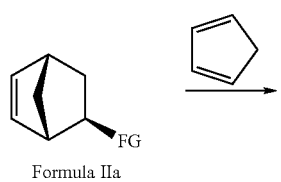
Formula IIa

-continued

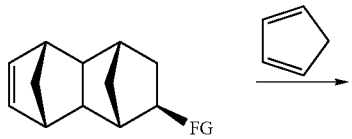

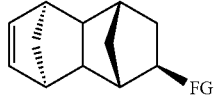
and similar stereoisomers

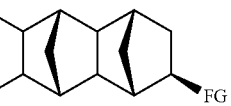

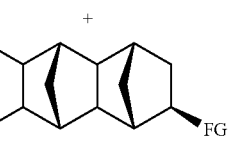
and similar stereoisomers

Formula IIb

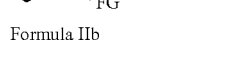

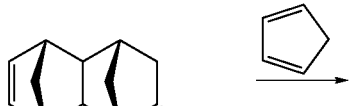

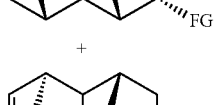
and similar stereoisomers

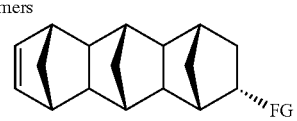

and similar stereoisomers

Referring now the Reaction Schemes that follow, it has been found advantageous to generate 5-norbornenecarbonitrile (5-NBCN or NBCN) as a first step to the forming of high purity exo-NBFG and endo-NBFG monomers. The Diels-Alder reaction to form the NBCN is thus shown as Step 1 of the Reaction Schemes. The benefit of such a first step is first, such a reaction results in a diastereomeric mixture having a ratio of endo to exo isomers of about 55:45 so that, advantageously, about equal amounts of each isomer is present in the mixture; and second that while most diastereomeric mixtures are difficult to separate, the NBCN isomers (also referred to herein as diastereomers or epimers) can be successfully separated by fractional distillation. It should be noted that the conditions under which such a distillation is performed should be carefully controlled such that the separation can be cost effective and high yielding both with regard to the starting ratio of isomers and with regard to the isomeric purity of the individual endo- and/or exo-isomers.

Once the individual endo- and exo-NBCN isomers are separated, each can be reduced to the analogous endo- or exo-norbornene-5-carboxaldehyde isomer (Step 2), for example by partial reduction to an imine and hydrolysis to the aldehyde. In general, this method involves using a metal hydride reducing agent to add 1 mol of hydrogen for the reduction to the imine and hydrolysis, in situ, to form the aldehyde. Appropriate reducing agents include, but are not limited to, lithium aluminum hydride ($LiAlH_4$), alkyl aluminum hydrides (e.g. diisobutylaluminum hydride (DIBAL-H)), alkoxyaluminum hydrides (e.g. lithium triethoxyaluminum hydride ($LiAlH(OEt)_3$)), and dialkylamino lithium hydrides (e.g. lithium tris(diethylamino)aluminum hydride ($LiAlH(NEt_2)_3$)). As shown in Steps 3-13 of the Reaction Schemes, first forming either a desired exo- or endo-5-carboxaldehydeNB (NBCHO) provides an advantageous starting point for the forming of a broad range of exo- and endo-NBFG monomers.

For ease of understanding and display, such Reaction Schemes depict only the exo-NBFG monomer for each step (except for Step 13 where only the endo isomer has, to date, been formed), however it will be understood that where the endo-NBCHO is used as a starting point, the NBFG monomers formed will be an endo-monomer. In the Examples included herein, an exemplary reaction for each of Steps 1-13 is provided. It should be noted that these exemplary reactions are non-limiting as the use of reagents other than those disclosed can also be effective for forming a desired essentially pure exo- or endo-NBFG monomer.

Still referring to the Reaction Schemes, the advantage of forming the NBCHO epimers from the analogous NBCN epimers should be recognized as (1) forming NBCN via a Diels-Alder reaction provides nearly equal amounts of each isomer, (2) the separation of such NBCN isomers can be effectively accomplished via distillation, and (3) the reduction of such NBCN isomers to the corresponding NBCHO isomer using an appropriate aluminum hydride is essentially quantitative. Further to this advantage is that the resulting NBCHO isomers are readily transformed to the corresponding carboxylic acid (via an appropriate oxidizing reagent) or alcohol (via an appropriate hydride donor reagent) thus providing facile pathways to a wide variety of functionalized NB monomers without losing the isomeric purity obtained through the initial separation of the NBCN isomers. In contrast the direct acid or base treatments of nitriles to form the analogous carboxylic acids generally results in the epimerization of the diastereomers. Therefore, embodiments in accordance with the present invention provide a significant advantage in comparison with previously known methods.

Said in a different manner, embodiments in accordance with the present invention allow for forming either an alcoholic functionalized NB monomer of high isomeric purity or a carboxylic acid functionalized NB monomer of high isomeric purity. Such alcoholic functionalized monomers can be used to form derivatives having functional groups such as —$CH_2OAc$, —$CH_2OCH_2C(CF_3)_2OH$ (via hexafluoroisobutylene oxide), —$CH_2Cl$, —$CH_2Br$, —$CH_2I$, —$CH_2NH_2$, —$CH_2OMs$, —$CH_2OTs$ and —$CH_2C(CF_3)_2OH$. In addition, such embodiments provide for the use of a variety of coupling reactions to expand the above list of possible functional groups significantly, such reactions including, but not limited to, the Kumada, Sonogashira, Heck, Stille, Suzuki, Hiyama and Negishi reactions. Further, the carboxylic acid functionalized isomers can be subjected to standard organic synthesis derivatization methods to generate ester functionalized materials, for example, some of the materials shown above as Structures MM. Still further where an alcoholic functionalized isomer is converted to a chloro, bromo or iodo diastereomer, such can be employed in $sp^3$-sp, $sp^3$-$sp^2$, and $sp^3$-$sp^3$ coupling and organometallic reactions (e.g. formation of Grignards, organo lithiums, organo zincs, organo cuprates and organo stannanes). In one particular noteworthy example, exo-$NBCH_2I$ (or endo-$NBCH_2I$) can be used to generate an organozinc iodide at moderate temperatures. Advantageously, it has been found that such an organozinc iodide reacts smoothly with hexafluoroacetone to generate the appropriate exo- or endo-HFANB in high yield (about 70%) and high diastereomeric purity.

While not specifically shown, embodiments in accordance with the present invention encompass a homologation reaction of an essentially pure exo- or endo-NBFG that provides for an overall increase of the carbon skeleton of the functional group. For example where the FG is an aldehyde or ketone, a reaction with diazomethane or methoxymethylenetriphenylphosphine effectively inserts a methylene (—$CH_2$—) unit in the hydrocarbon chain of the FG providing the next homolog. Other exemplary homologation reactions that are encompassed by embodiments of the present invention include, among others, (i) Seyferth-Gilbert homologation, i.e., displacement of a halide by a cyanide group, which can be reduced to an amine; (ii) Wittig reaction of an aldehyde with methoxymethylene triphenylphosphine, which produces a homologous aldehyde; (iii) Arndt-Eistert synthesis is a series of chemical reactions designed to convert a carboxylic acid to a higher carboxylic acid homolog (i.e., contains one additional carbon atom) and (iv) Kowalski ester homologation which is a chemical reaction for the homologation of esters. For some embodiments of the present invention, reactions that increase the chain length of the FG by more than one unit can also be employed. For example, the nucleophilic addition of ethylene oxide results in a ring-opening that produces a primary alcohol with two extra carbons.

The endo and exo-NBFG monomers that are useful in such homologation reactions are $NBCH_2X$ (X=Br, Cl, I, OMs, and OTs), $NBCO_2R$, $NBCO_2H$, $NBCH_2OH$, and $NBCH_2C(O)R$, and NBCN. Specifically, exo-$NBCO_2H$ can be converted to exo-$NBCH_2CO_2H$ which in turn can be reduced to exo-$NBCH_2CH_2OH$, which can be employed in preparing exo-$NBCH_2CH_2FG$ monomers.

Thus, embodiments in accordance with the present invention encompass the forming of diastereomerically pure carboxaldehyde building blocks (e.g. exo-NBCHO and endo-NBCHO, which can be transformed into a multitude of derivatives that are important for polymer applications and small molecule transformations. The organic transformations of functional groups into new functional groups include, among others, oxidation, reduction, homologation, Wittig, amination, reductive aminations, esterification, hydrogenation, hydrolysis, alcoholysis (acetal formation), condensation (e.g. aldol), alkylation, arylation and transition metal catalyzed reactions. However, it should be noted that while there are a large number of common organic transformations that can be employed by embodiments in accordance with the present invention, not all such transformations are effective; hence judicious choice of reaction conditions and reagents is necessary to preserve the nature of the norbornene double bond for use in a subsequent polymerization. Where a specific transformation method or product is desired, but would be likely to effect the nature of the norbornene double bond, it has been found that the use of protecting groups at the double bond can be effective to allow completion of the desired transformation, Further still, it should be noted that embodiments in accordance with the present invention also encompass the separation of the diastereomeric mixtures of bis-nitrile norbornenes, TDCN diastereomeric mixtures and such mixtures of higher homologs of such norbornenes, for example where m of Formula I is 3 or greater. Thus the transformations depicted in the Reaction Schemes are generally representative for analogous bis-nitrile and TD and higher materials.

Referring still to bis-norbornenecarbonitrile diastereoisomers such exo- and endo-norbornene-type monomers are exo,exo-norbornene-2,3-dicarbonitrile, exo,endo-norbornene-2,3-dicarbonitrile, and endo,endo-norbornene-2,3-dicarbonitrile, appropriately represented by Formulae IIIa and IIIb and IIIc, respectively:

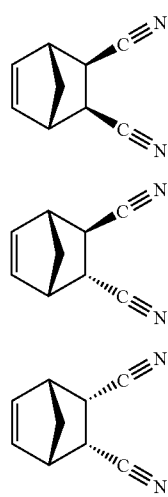

Formula IIIa

Formula IIIb

Formula IIIc

Representative preparative methods of the pure diastereomers of formulae IIIa, IIIb, and IIIc are described in the following articles: (i) *A contribution to the stereospecificity of [4+2]cycloadditions*, Prantl, et al. Tetrahedron Letters (1982), 23(11), 1139-42, (ii) *Facile preparation of trans-2,3-bis[(t-butylamino)methyl]norbornene*. Wynne, et al. Organic Preparations and Procedures International (2002), 34(6), 655-657, and (iii) *Bromine addition to cyanonorbornene derivatives*. Kikkawa, et al. Bulletin of the Chemical Society of Japan (1972), 45(8), 2523-7.

It should be noted that since embodiments in accordance with the present invention can readily provide both diastereomeric forms of a large variety of functionalized norbornene-type monomers appropriate planning of the polymerization of such monomers, makes it possible to provide specific ratios of diastereomers to the polymerization reaction (by mixing the pure diastereomers). Thus, ones ability to tailor the properties of the resulting polymer is enhanced as compared to not having such pure diastereomers. For example, U.S. Pat. No. 7,341,816, entitled "Method of Controlling the Differential Dissolution Rate of Photoresist Compositions, Polycyclic Olefin Polymers and Monomers Used for Making Such Polymers" to Rhodes, et al., teaches that the dissolution rate of some polymers is related to the exo/endo ratio of functionalized polymer repeating units. Such patent shows that polymers having a high concentration of repeating units derived from exo-HFANB exhibit a higher than expected dissolution rate in aqueous base solutions than analogous polymers that have a lower concentration of repeating units derived from exo-HFANB, the comparative polymers having essentially the same molecular weight. Where such patent teaches obtaining polymers of different isomeric ratios by separating them via a distillation, embodiments of the present invention provide for providing a specific ratio of isomers to the polymerization such that the resultant polymer has a desired characteristic (e.g. a high dissolution rate or a low dissolution rate).

EXAMPLES

The following examples are provided for illustrative purposes only and are in no way restrictive or limiting with respect to the scope and spirit of the embodiments in accordance with the present invention that are claimed. Specific examples are provided that demonstrate the formation of each of the monomers shown in the Reaction Schemes above, as well as examples that demonstrate further demonstrate the broad scope of the instant invention. Further, for each of the following examples, the GC analysis was done on a DB5 column, 30 meters in effective length and having a 0.32 mm ID and a 0.25 µm film. The sample was injected into an injection chamber maintained at 275° C. After injection the column was maintained at 55° C. for one minute and then heated to 170° C. @ 5° C./min. The detector temperature was 325° C. Specific retention times are reported below where appropriate.

Preparation of exo-/endo-Norbornenecarbonitrile (exo-/endo-NBCN)

To a 20 liter Parr pressure-rated reactor flushed with $N_2$, 6.8 kg (51.3 mol, 1.1 eq of cyclopentadiene) of dicyclopentadiene was added. Next, 5.11 kg (96.3 mol, 1.0 eq) of acrylonitrile was added. The reactor was flushed three times with $N_2$, and then heated over a period of 3.25 hours to a temperature of about 180° C. It was observed that the pressure reached a peak of about 100 psig during the initial 3.25 hours. The reaction mixture was stirred for another 2 hours at about 180° C. during which time the pressure stabilized to about 11 psig. After cooling to 25° C., 11.81 kg of the reaction mixture was drained from the reactor. GC analysis of the mixture indicated a 93.0% yield of exo/endo norbornene carbonitrile (43.3%/56.6%) product. GC retention time was 4.0 min. (exo-NBCN), 4.7 min. (endo-NBCN).

Separation/Purification
exo-/endo-Norbornenecarbonitrile

About 8 kg of exo/endo norbornene carbonitrile (NBCN) was charged to a vacuum distillation apparatus consisting of an appropriately sized still pot with heating mantle, a packed distillation column (60 theoretical plates), a reflux splitter, a water cooled condenser, a condensate receiver and a vacuum pump. The still pot temperature was controlled by adjusting the heat input to the heating mantle and system vacuum was controlled by adjusting the vacuum pressure at the overhead receiver (see Experimental Section below).

After transferring the NBCN to the still pot, the distillation system vacuum was adjusted to the desired set point. Heating of the still pot then proceeded until total reflux conditions were established in the distillation column. The reflux splitter was then started at the desired reflux ratio and fractional distillation proceeded by periodically removing liquid fractions from the overhead receiver. GC analysis was used to determine composition of the overhead liquid fractions. Distillation reflux ratio was adjusted as needed to affect composition of the overhead stream. The initial overhead fractions were enriched in "light" components, which were primarily acrylonitrile (ACN), cyclopentadiene (CPD) and dicyclopentadiene (DCPD). After removal of these "light" components, high purity exo-NBCN was then separated from the remaining endo-NBCN. After removal of "transition" fractions, high purity endo-NBCN was then collected. The distillation process is terminated once the majority of endo-NBCN has been removed from the still pot.

TABLE 1

| Feed NBCN (exo:endo ratio = 1:3) | | |
|---|---|---|
| Still Pot Temperature: | exo-NBCN 127° C. | endo-NBCN 125° C. |
| Overhead Temperature: | exo-NBCN 57° C. | endo-NBCN 85° C. |
| System Vacuum: | exo-NCNB 2.0 mmHg | endo-NBCN 1.7 mmHg |
| Reflux Ratio: | exo-NBCN 30:1 | endo-NBCN 5:1 |

Approximately 57% of the contained exo-NBCN in the starting mixture was removed as high-purity (98% or greater) material. Approximately 44% of the contained endo-NBCN in the starting mixture was removed as high-purity (98% or greater) material. The medium-purity fractions can be recycled to increase overall process yields.

Preparation of Exo-Norbornene-5-carboxaldehyde
(Exo-NBCHO)

A 12-Liter glass flask fitted with mechanical stirrer, nitrogen gas inlet, thermowell, and septa-sealed addition funnel was dried by heating to ~120° C. under a nitrogen flush. The flask was cooled to room temperature before cannulating 7900 ml (11.79 moles) 1.5 M Diisobutylaluminum hydride (DIBAL-H) in toluene via the addition funnel into the flask. The DIBAL-H solution was cooled to −51.6° C. before adding exo-NBCN (1328 g, 11.14 mol) dropwise. The addition was completed within 2 hrs 24 min while the temperature ranged from −51.6 to −39.3° C. The mixture was stirred an additional 30 minutes. GC analysis revealed no unreacted exo-NBCN remaining. The reaction mixture was kept at −46 to −39° C. while it was cannulated in eleven 500-ml portions into a dry ice/isopropanol-cooled jacketed addition funnel. This was added rapidly dropwise in eleven 500-ml portions to mechanically stirred 12.24 Liters of 3.5 N hydrochloric acid chilled to −5.6° C. with dry ice/acetonitrile. There is an induction period, so the reaction exotherm was allowed to subside before each subsequent addition of the DIBAL-H reaction mixture. The temperature ranged from −5.6 to +0.1° C. Quench time was 2 hours. MTBE (methyl tertiary butyl ether, 4000 ml) was added via the chilled addition funnel. The mixture was stirred several minutes, allowed to settle, and the phases separated. The aqueous phase was extracted with 3×4000 ml MTBE. The organic portions were combined, washed with 5000 ml 3.5 N hydrochloric acid, and washed with 3×2 gallons brine until the final wash gave pH 6. The MTBE/toluene solution was split and placed in seven bottles, dried over sodium sulfate, and stored in a refrigerator overnight. The mixture was filtered and rotary evaporated at 35° C. maximum bath temperature to yield 3173 g of product. NMR analysis indicates 35.2 wt % NBCHO in toluene, giving 82% yield. GC analysis gives an exo/endo ratio of 99.8/0.2. NBCHO is unstable and epimerizes readily, therefore the solution was refrigerated for future use. GC retention time was 2.05 min. (exo-NBCHO), 2.23 min. (endo-NBCHO).

Preparation of Exo-Norbornene-5-methanol
(Exo-NBCH$_2$OH)

In a 22-Liter glass flask fitted with mechanical stirrer, thermowell, nitrogen inlet, and addition funnel were placed 1880 ml of 8% aqueous sodium hydroxide solution. NaBH$_4$ (174.1 g, 4.6 mol) was added portion wise. The mixture was cooled to −7.4° C. Exo-NBCHO (3173 g at 35.2 wt % in toluene, ~9.17 mol total) was dispensed just before use in 400 ml portions that were dissolved in 600 ml methanol before adding dropwise to the sodium borohydride solution. Addition time totaled 5.1 hours while reaction temperature ranged from −7.1 to −0.8° C. Inconsistent GC analysis prompted the addition of another 35 g of sodium borohydride. The reaction was stirred one hour while cooling from −1.7 to −12.7° C. GC analysis indicated <0.15% unreacted NBCHO. 10% aqueous sulfuric acid (2200 ml) was added dropwise over 1.5 hours while the temperature ranged from −11.4 to +0.7° C. Resulting pH was 6. Dichloromethane (3000 ml), 500 ml brine, and 2000 ml water were added and the mixture stirred several minutes. The phases were separated. The remaining aqueous phase was treated with 2000 ml dichloromethane, 2000 ml water, and 2000 ml brine. The dichloromethane phase was removed and the aqueous phase again mixed with 2000 ml dichloromethane, 2000 ml water, and 2000 ml brine. The dichloromethane phase was removed and the aqueous phase treated with 2000 ml dichloromethane and 2000 ml water. The dichloromethane extracts were combined, the residual water was separated, and the organic portion then dried over sodium sulfate overnight. After filtration, the extracts were rotary evaporated to give 1210 g yellow liquid (87% yield from NBCHO).

The material was vacuum distilled, giving the following fractions:

I. 34.6-109.4° C. (12-20 Torr), 46.2 g, hazy, 60.3% NBMeOH and 39.7 wt % toluene II. 106.3-100.7° C. (5-8 Torr), 172.5 g, 98.5% exo-NBMeOH, 1.3% endo-NBMeOH, no toluene III. 81.4-93.2° C. (2-3 Torr), 236.7 g, 99.3% exo-NBMeOH, 0.7% endo-NBMeOH, no toluene IV. 62.2-69.4° C. (1-2 Torr), 578.1 g, 99.1% exo-NBMeOH, 0.9% endo-NBMeOH V. 63.1-68.5° C. (1 Torr), 29.02 g, 99.5% exo-NBMeOH, 0.5% endo-NBMeOH.

The distillation pot residue was dissolved in ~400 ml dichloromethane and washed with 100 ml 10% sulfuric acid. The resulting mixture was treated with 100 ml water to force phase separation. The phases were separated. To the aqueous phase was added 100 ml brine to force more dichloromethane out of the solution. The dichloromethane portions were combined, washed with 5×100 ml brine to pH 6, and then dried over sodium sulfate. The dried extract was filtered and rotary evaporated. This product was vacuum distilled to give 37.7 g @ 60.8-65.1° C. (1 Torr). GC analysis showed 0.5% endo-isomer and 99.5% exo-isomer. A less pure fraction of 37.31 g was collected at 63.1-65.2° C. (2 Torr) containing 98.9% exo-isomer and 0.85% endo-isomer. Total yield of >99.8% (total isomer) purity was 1058.5 g (76.5% yield from NBCN, ~93% yield from NBCHO). GC retention time: 2.82 minutes (endo-NBMeOH), 3.97 min (exo-NBMeOH).

Preparation of endo-Norbornenecarboxaldehyde
(endo-NBCHO)

A 12-Liter glass flask fitted with mechanical stirrer, nitrogen gas inlet, thermowell, and septa-sealed addition funnel was dried by heating to ~120° C. under a nitrogen flush. The flask was cooled to room temperature before cannulating 4970 ml (7.4 moles) 1.5 M DIBAL-H in toluene via the addition funnel into the flask. The DIBAL-H solution was cooled to −71.8° C. Endo-NBCN (838 g, 7.0 mol) was melted, diluted with 100 ml toluene, and added dropwise to the DIBAL-H solution. The addition was completed within 2 hours while the temperature ranged from −71.8 to −50.4° C. GC analysis revealed no unreacted endo-NBCN remaining. The reaction mixture was cannulated in ten 500 ml portions into a dry ice/isopropanol-cooled jacketed addition funnel. Each portion was then added dropwise to 8190 ml of a mechanically stirred 3.5 N hydrochloric acid solution chilled to −15.5° C. with dry ice/acetonitrile. An induction period was observed, so the reaction exotherm was allowed to subside before each subsequent addition of the DIBAL-H reaction mixture. During these additions, the temperature ranged from −35 to +1.0° C. Total quench time was about 2 hours. Next, MTBE (3000 ml) was added via the chilled addition funnel, the mixture stirred for several minutes, allowed to settle, and the phases separated. The aqueous phase was extracted with 2×3000 ml MTBE. The organic portions were combined, washed with 2500 ml 3.5 N hydrochloric acid, and then washed with 7×1 gallon brine until the final wash showed a pH of 7. The MTBE/toluene solution was split into four portions and each was dried over sodium sulfate, and stored in an ice chest overnight.

The next day, the mixture was filtered and rotary evaporated at a maximum bath temperature of 35° C. NMR analysis of the residues indicated 25.0 wt % NBCHO in toluene with 9.2 wt % residual MTBE. The product was concentrated further with rotary evaporation and a second NMR analysis indicated 31.7% endo-NBCHO, 65.4% toluene, and 2.8% MTBE. GC analysis indicated the endo-/exo-ratio to be 97.3/2.7. Yield was approximately 70%. Since endo-NBCHO is unstable and epimerizes readily, the solution was refrigerated until needed. GC retention time: 2.13 minutes (exo-NBCHO), 2.33 (endo-NBCHO).

Preparation of endo-Norbornenemethyl Alcohol (endo-NBCH$_2$OH)

In a 5-L 4-neck flask fitted with mechanical stirrer, thermowell, nitrogen inlet, and addition funnel were placed 360 ml (0.72 mol) of 8% aqueous sodium hydroxide solution. NaBH$_4$ (33.1 g, 0.88 mol) was added portionwise. The mixture was cooled to −10.6° C. Approximately one-half of endo-NBCHO solution (558.1 g at 30.6 wt % in toluene, ~1.39 mol total) was diluted with 500 ml methanol and added dropwise. Addition time was 1.5 hrs while reaction temperature ranged from −11.4 to −3.1° C. The remaining endo-NBCHO solution was diluted with 500 ml methanol and added dropwise to the reaction mixture. Addition was completed in 48 minutes with reaction temperature ranging from −10.8 to −6.3° C. GC analysis indicated 4.9% endo-NBCHO remained. The mixture was stirred at −11.8 to −5.6° C. for 5 hrs 21 min. which allowed the endo-NBCHO content to drop to 1.6%. Another 3.22 of sodium borohydride was added and the mixture stirred another 1.5 hrs at −5.3 to −13.5° C. GC analysis showed 1.0% endo-NBCHO remaining. The reaction flask was packed in ice and the mixture allowed to stir overnight. The temperature had climbed only to 3.5° C. and GC analysis showed that only 0.4% endo-NBCHO remained.

The reaction was cooled to −11.5° C. and 10% aqueous sulfuric acid (390 ml) was added dropwise over 1.5 hrs while the temperature ranged from −11.5 to +0.7° C. At the end of the addition the pH was 7. Another 100 ml of 10% sulfuric acid was added to bring the pH to 2. Dichloromethane (500 ml) was added and the mixture stirred vigorously. 100 ml brine and 300 ml water was added, mixed thoroughly, and then allowed to settle. A large emulsified interface resulted. The dichloromethane portion was separated. Then 500 ml dichoromethane, 100 ml brine, and 300 ml water were added to remaining aqueous phase. After mixing, the dichloromethane phase was collected. Another 500 ml dichloromethane, 100 ml brine, and 300 ml water was added to aqueous phase and mixed. The dichloromethane phase was again collected. The emulsion phase was collected and allowed to separate. The resulting aqueous phase was removed and the remaining emulsion treated with 500 ml brine. This gave a clean separation of phases. The dichloromethane phase was removed, washed with 200 ml brine to pH 6, and then combined with the previous dichloromethane extracts. The combined dichloromethane extracts were washed with 3×400 ml brine to pH 7, dried over sodium sulfate, filtered and rotary evaporated to 331.6 g. NMR indicates this is 59 wt % endo-NBMeOH in toluene. NMR shows only a trace of exo-isomer. GC analysis indicates an endo/exo ratio of 99:1.

The material was vacuum distilled through a 12-inch Vigreux column, giving the following fractions:

I. 25.1-19.0° C. (1.3-1.6 Torr), 11.86 g, 99.5% toluene

II. 73.8-66.9° C. (1.20-1.15 Torr), 28.79 g, 98.3% endo-NBMeOH, contains 0.09% toluene III. 65.3-63.1° C. (1.25-1.20 Torr), 99.64 g, 99.2% endo-NBMeOH, no toluene IV. 58.6-44.3° C. (1.20-0.53 Torr), 47.87 g, 99.8% endo-NBMeOH V. 47.2-42.2° C. (0.62-0.57 Torr), 2.89 g, 99.4% endo-NBMeOH.

Total yield of >99% endo-NBMeOH was 150.4 g (87%). Yield based on endo-NBCN was 58%. NMR indicates 99.5% endo. GC Retention time: 4.565 minutes (endo-NBMeOH), 4.599 minutes (exo-NBMeOH).

Preparation of Exo-Norbornenemethyl Acetate (exo-NBMeOAc)

A 12-Liter glass flask, fitted with mechanical stirrer, nitrogen inlet, addition funnel, and thermowell, was dried with a hot air gun to 120° C. under a nitrogen flush. After cooling to room temperature, exo-norbornenemethanol (500.2 g, 4.0 mol) was placed in the flask, followed by 4 Liters dry dichloromethane, 988 g (12.5 mol) dry pyridine, and another 2 Liters dry dichloromethane. Dimethylaminopyridine (2.0 g, 16.5 mmol) was added. Acetic anhydride was added rapidly within 30 minutes, causing the reaction temperature to rise from 24° C. to 41° C. After 10 minutes, GC analysis indicated only 1.7% starting material remained. After 2.5 hours, only 0.3% starting material remained. An additional 22 ml of acetic anhydride was added and the reaction mixture was allowed to stir overnight at room temperature. GC analysis showed no further change in product composition. The reaction was rotary evaporated to remove dichloromethane and then rotary evaporated at 80° C. to remove excess pyridine and acetic anhydride. The residue, totaling 553 g, was vacuum distilled giving three fractions:

I: 33.5° C. (2 Torr)-67.1° C. (<2 Torr), 22.8 g, 54 wt % (NMR) NBMeOAc, 13 wt % pyridine, 33 wt % acetic anhydride II: 68.4-61.0° C. (<2 Torr), 501.5 g, 99.7% exo-NBMeOAc III: 59.4-60.4° C. (<2 Torr), 19.8 g, 99.5% exo-NBMeOAc. NMR showed an extra signal at 3.05 ppm.

Yield was 501.5 g (75% of theoretical). GC retention time: 4.51 minutes, exo-NBMeOAc.

Preparation of Endo-Norbornenemethyl Acetate (endo-NBMeOAc)

A 3-Liter glass flask, fitted with mechanical stirrer, nitrogen inlet, addition funnel, and thermowell, was dried with a hot air gun to 108° C. under a nitrogen flush. After cooling to room temperature, endo-norbornenemethanol (125.0 g, 1.0 mol) was placed in the flask, followed by 4 Liters dry dichloromethane, 247 g (3.1 mol) dry pyridine, and another 500 ml dry dichloromethane. Dimethylaminopyridine (0.5 g, 4.2 mmol) was added. Acetic anhydride was added rapidly dropwise within 18 minutes, causing the reaction temperature to rise from 24° C. to 38.7° C. After 34 minutes, GC analysis indicated only 1.8% starting material remained. After 2 hours, no significant quantities of starting material remained. The reaction mixture was allowed to stir overnight at room temperature. GC analysis showed no further change in product composition. The reaction was rotary evaporated to remove dichloromethane and then rotary evaporated at 60° C. to remove excess pyridine and acetic anhydride. NMR analysis indicated that the residue, totaling 165.6 g, still contained 4.3 wt % pyridine. The material was washed with 250 ml distilled water, causing the lower organic phase to become very milky. Dichloromethane (100 ml) was added to the aqueous phase, mixed, and the phases separated. The organic phases were combined and washed with 10% aqueous sulfuric acid. This caused the organic phase to clear. A wash with 250 ml brine caused a phase reversal, leaving the organic phase on top. The organic phase was washed with 3×250 ml brine to a final wash pH of 6. The organic phases were dried over sodium sulfate, filtered, and rotary evaporated to give 156.5 g. NMR and GC analysis showed no pyridine remained. The product was vacuum distilled giving four fractions:

I. 28.6° C. (6 Torr)-58.8° C. (1.95 Torr), 5.8 g, 98.4% endo-NBMeOAc (GC)
II. 55.2° C. (1.90 Torr)-49.2° C. (1.50 Torr), 125.2 g, 100% endo-NBMeOAc
III. 48.9° C. (1.50 Torr)-50.6° C. (1.50 Torr), 8.9 g, 100% endo-NBMeOAc
IV. 51° C. (1.50 Torr), 0.8 g, 100% endo-NBMeOAc Total product was 140.7 g for 84% yield. GC retention time: 3.75 minutes, endo-NBMeOAc.

Preparation of endo-Norbornenemethylmethanesulfonate (endo-NBMeOMs)

Endo-5-(2-hydroxymethyl)norbornene (104.79 g, 0.85 mol), 485 ml dichloromethane, and methanesulfonyl chloride (100.99 g, 0.88 mol) were placed in a 4-neck 3-L flask fitted with mechanical stirrer, thermowell, nitrogen inlet, and addition funnel. 240 ml dichloromethane was added to rinse in the methanesulfonyl chloride. The stirred mixture was chilled to −11.1° C. Triethylamine (101.26 g, 1.00 mol) was added rapidly dropwise over a 2 hr period with the temperature ranging from −11.1 to +7.0° C. The resulting yellow slurry was allowed to warm to 18.9° C. during 78 minutes. GC analysis indicated 0.3% unreacted starting material remaining. An additional 3.82 g of methanesulfonyl chloride was added and the mixture allowed to stir overnight at room temperature. GC analysis indicated that 0.1% starting material remained. Five hundred ml water was added to clear the solution. The phases were separated. The dichloromethane portion was washed with 450 ml of 1 N HCl and then washed with 4×1000 ml brine to a wash pH=6. The dichloromethane solution was dried over sodium sulfate, filtered, and rotary evaporated to 185.15 g liquid (>100% yield). GC analysis gave mesylate content at 98.1%. NMR analysis indicated 7.5 wt % dichloromethane remaining. Endo/exo ratio was 99.1: 0.9.

Preparation of endo-5-(2-Iodomethyl)norbornene (endo-NBMeI)

Endo-Norbornenemethylmethanesulfonate (185.15 g, 92.5%, 0.85 mol) and 1500 ml 2-pentanone were placed in a 4-neck 5-L flask fitted with mechanical stirrer, condenser with nitrogen inlet adapter, stopper, and thermowell. The mixture was mixed well before adding 190.4 g (1.27 mol) sodium iodide and 200 ml 2-pentanone. The mixture was heated to reflux. After 1.5 hrs reflux, the mixture became very thick and was diluted with an additional 500 ml 2-pentanone. After another 1.5 hrs at reflux, another 500 ml of 2-pentanone was added. The mixture continued to thickened and began to splash solids over the upper portions of the reaction flask. An additional 250 ml 2-pentanone were added and the reaction cooled from 100.9° C. to 95-96° C. to permit smoother stirring. The reaction was allowed to continue overnight at 95-96° C., then heated to 100.4° C. for 2 hrs when GC analysis indicated no starting material remained. Total reaction time at >90° C. was 25 hrs. The reaction was allowed to stir and cool to 30° C. Water (500 ml) was added to clear the solution. The phases were separated. The aqueous phase was extracted with 500 ml and 250 ml of ethyl acetate. The ethyl acetate extracts were combined with 2-pentanone phase and rotary evaporated at <35° C. to give 226.7 g red oil. This was diluted with 300 ml dichloromethane and washed with 2×200 ml 10% aqueous sodium bisulfite. The organic phase was then washed with 300 ml brine, 300 ml saturated sodium bicarbonate, and 350 ml brine to final wash pH=7. The dichloromethane solution was dried over sodium sulfate, filtered, and rotary evaporated to 203.6 g. Water (15 ml) was added and the mixture rotary evaporated until the residual pentanone was removed and only water began to distill over. The residue was dried over sodium sulfate, filtered, and rinsed with dichloromethane. This was vacuum distilled through a 12-inch Vigreux column, giving:

1. 42.1-50.3° C. (1.35-1.40 Torr), 21.88 g, 88.3% endo-NBMeI
2. 46.5° C. (1.25 Torr)-42.5° C. (1.20 Torr), 58.37 g, 99.0% endo-NBMeI
3. 43.3-39.7° C. (1.15-1.20 Torr), 79.19 g, 99.5% endo-NBMeI
4. 40.0-34.9° C. (1.15 Torr), 1.53 g, 98.3% exo-NBMeI.

Yield of >99.0% endo-NBMeI was 137.56 g (69%).

Preparation of Exo-α,α-bis(trifluoromethyl)bicyclo [2.2.1]hept-5-ene-2-ethanol (Exo-HFANB)

A 12-L 4-neck flask fitted with mechanical stirrer, dry ice condenser, thermowell, and nitrogen inlet valve was heated and hot air-dried to 110° C. under a nitrogen flush. After cooling to 32° C., zinc dust (Alfa Aesar A13633, 222.52 g, 3.45 mol) and then 2000 ml DrySolve dimethylacetamide was placed in the flask. Next, Iodine (59.33 g, 0.23 mol) was placed in the flask, followed by a rinse with 300 ml DrySolve dimethylacetamide. Within 7 minutes, the initially formed reddish color changed to green and then to gray as the mixture warmed to 33.3° C. NBMeI (539.54 g, 2.3 mol) was added all at once. The mixture was heated to 79° C., when the reaction initiates an exotherm, causing the temperature to rise to 115°

C. The heat source is removed and the reaction allowed to cool back to 89° C. Heating is resumed. After one hour at >79° C., GC analysis shows no starting material remaining. The reaction is cooled to −26.6° C. with an acetonitrile/dry ice cooling bath. HFA (466.1 g, 2.77 mol) was condensed into the reaction mixture. The initial addition of HFA caused a temperature rise from −28 to −19.1° C. The cooling bath was drained and replaced with a wet isopropanol/dry ice cooling bath. The reaction mixture was stirred at −18.5 to −1.7° C. for 5.3 hours. The mixture was chilled back to −28° C. before adding distilled water carefully in 200 to 500 ml increments up to a total water volume of 3000 ml. An additional 1000 ml of water was added. The entire mixture was poured into 4000 ml water. The zinc residues in the reaction flask were treated with 1600 ml 3.5 N HCl and the resulting mixture combined with the previous aqueous quench. The reaction flask was rinsed further with ~3.5 L water. The combined aqueous quenches were extracted with 3×4000 ml cyclohexane. The cyclohexane extracts were combined and washed with 1 gal brine to pH 7. After storing overnight under nitrogen, the cyclohexane solution was extracted with 3×500 ml 25% aqueous tetramethylammonium hydroxide (TMAOH). The combined TMAOH extracts were washed with 3×1000 ml cyclohexane and then acidified with 400 ml concentrated HCl. The lower phase was separated to collect 657.09 g of crude HFANB. NMR analysis showed this contained 10.5 wt % dimethylacetamide (DMA).

The crude product was washed with 200 ml 31.5% aqueous sulfuric acid. No phase separation resulted so the mixture was diluted 1000 ml dichloromethane to force a slow phase separation. The organic phase was washed with 2×200 ml 31.5% sulfuric acid and then with 2×400 ml 31.5% sulfuric acid until NMR analysis showed <0.3 wt % DMA remaining. The product solution was washed with 500 ml brine, 500 ml saturated sodium bicarbonate, 2×500 ml brine, and with 500 ml brine containing 10 ml 3.5 N HCl until the final wash pH=7. The product solution was dried over sodium sulfate, filtered, and rotary evaporated. The residue was distilled through a 14-inch Vigreux column. The following fractions were collected:

I. 42.6-49.5° C. (2 Torr), 44.03 g, 99.2% (GC)
II. 45.6-44.8° C. (1.95 Torr), 168.83 g, 98.8% (GC)
III. 41.5-43.9° C. (1.90 Torr), 127.44 g, 99% (GC)
IV. 41.5-43.2° C. (1.85 Torr), 118.64 g, 99.3% (GC)
V. 40.2-45.0° C. (1.75-1.80 Torr), 14.65 g, 99.1% (GC), contains 0.4 wt % DMA (NMR)
VI. 44.9-49.9° C. (1.80 Torr), 3.10 g, 99.1% (GC), contains 0.8 wt % DMA (NMR)
VII. 51.8-63.3° C. (1.80 Torr), 7.55 g, 98.65% (GC), contains 4.4 wt % DMA (NMR)

High purity exo-HFANB (>99%), combined fractions I-IV, was 458.94 g for 73% yield.

Preparation of Endo-α,α-bis(trifluoromethyl)bicyclo[2.2.1]hept-5-ene-2-ethanol (Endo-HFANB)

A 3-L 3-neck flask fitted with mechanical stirrer, dry ice condenser, thermowell, and nitrogen inlet was heated and hot air-dried to ~105° C. under a nitrogen flush. After cooling to room temperature, zinc dust (Alfa-Aesar A13633, 57.70 g, 0.88 mol) was placed in the flask, followed by 500 ml Dri-Solve dimethylacetamide (DMA). The mixture was stirred as iodine (15.0 g, 0.059 mol) was added, followed by 100 ml dimethylacetamide rinse. The mixture fumes, warms to 32.3° C. and became green. After 3 minutes, the zinc slurry had turned back to blue-gray. After waiting an additional nine minutes, endo-NBMeI (137.56 g, 0.59 mol) was added all at once. The mixture was heated to 80° C. Upon reaching 80° C., the temperature suddenly climbed to 96° C. before subsiding after the heating source had been removed. The heating source was replaced after the temperature dropped to 86° C. After 1 hour, GC analysis showed no NBMeI remaining. The mixture was stirred an additional 30 min at >80° C. before cooling to −29.8° C. in an acetonitrile/dry ice cooling bath. Hexafluoroacetone (HFA) (120.5 g, 0.73 mol) was condensed into the reaction mixture. The temperature ranged from −30.7 to −23.4° C. during the 17 minute addition time. The cooling bath was replaced with a methanol/ice cooling bath. The reaction mixture was stirred at −27.9 to −1.2° C. for 4.25 hours when GC analysis indicated that the endo-methylnorbornene (NBMe) (from hydrolyzed NBMeZnI) to HFANB signal ratio had become constant. The mixture was chilled to −30.9° C. before adding deionized water carefully in 50, 100, and 250 ml increments up to a total water volume of 1500 ml. Maximum temperature reached was −2.2° C. The liquid was decanted from the zinc salts. 500 ml water and 450 ml 3.5N HCl was added to the zinc salts, thoroughly mixed, and then combined with the earlier decant. The combined aqueous mixture was extracted with 3×1000 ml cyclohexane. The cyclohexane extracts were washed with 1000 ml brine to pH 5. GC analysis showed 61.3% HFANB in the extracts.

The cyclohexane extracts were extracted with 210 ml 25% aqueous tetraammonium hydroxide (TMAOH). GC analysis indicated that 5.9% HFANB remained in the cyclohexane phase, so the cyclohexane solution was extracted with an additional 50 ml 25% TMAOH. This left only 1.8% HFANB in the cyclohexane phase. The TMAOH extracts were combined and washed with 3×500 ml cyclohexane. The aqueous phase was acidified with 100 ml concentrated HCl to pH 1. A lower phase totaling 117.15 g of 90.1% purity HFANB separated out. GC analysis also indicated 6.1% dimethylacetamide (DMA) adduct impurity. The crude HFANB was diluted with 250 ml dichloromethane and then washed with 2×100 ml 10% sulfuric acid, but GC analysis showed this was ineffective for removing the DMA adduct. The crude product was washed with 2×100 ml and 200 ml 31.5% sulfuric acid. GC analysis show no DMA adduct remained. The dichloromethane solution was washed with 4×500 ml brine to pH 5. The product solution was dried over sodium sulfate, filtered, and rotary evaporated to 92 g liquid with 96.9% purity. This was vacuum distilled through a 12-inch Vigreux column. The following fractions were collected:

I. 31.7-43.1° C. (1.55-1.95 Torr), 10.74 g, 99.3% endo (GC)
II. 39.5-35.6° C. (1.15-1.50 Torr), 25.82 g, 99.7% endo (GC)
III. 33.9-30.1° C. (1.20-1.10 Torr), 36.02 g, 99.7% endo (GC)
IV. 32.3-26.5° C. (0.87-0.89 Torr), 4.21 g, 99.1% endo (GC), 0.3% DMA adduct Total HFANB at >99% purity was 76.79 g for 48% yield. Fractions I, II, and III showed a prominent −70.7 ppm signal in the 19F NMR. These fractions were combined, diluted with 100 ml cyclohexane, and extracted with 2×100 ml 25% TMAOH. The TMAOH extracts were washed with 3×100 ml cyclohexane and then acidified with 50 ml concentrated HCl to pH<2. The product separated as the lower phase. This was removed, washed with 2×200 ml brine to pH 6, dried over sodium sulfate, filtered and rotary evaporated to 69.54 g. NMR analysis indicated <0.4% of the component giving the −70.7 ppm signal in the 19F NMR. This material was vacuum distilled through a 12-inch Vigreux column to give the following fractions:

B1 27.2-41.2° C. (4.50-4.75 Torr), 40 mg forerun
B2. 45.1-39.0° C. (2.25-3.00 Torr), 1.11 g, 99.5% endo (GC)
B3. 37.6-31.5° C. (1.05-1.20 Torr), 42.62 g, 99.6% endo (GC)
B4. 30.5-27.9° C. (0.82-1.05 Torr), 21.87 g, 99.6% endo (GC).

19F NMR analysis showed little or no −70.7 ppm signal in fractions B3 and B4. Fractions B3 and B4 totaled 64.49 g for 40% yield. GC Retention time: 4.55 min (endo-HFANB), 4.43 min (exo-HFANB), 2.09 min. (endo-NBMe), 2.66 min (DMA adduct).

Preparation of Exo-Norbornenecarboxylic Acid (exo-NBCO$_2$H) (via AgNO$_3$ and NaOH)

Exo-NBCHO (1188 g of 49.2 wt % in toluene, ~4.79 mol) was placed in a 50-Liter glass flask fitted with mechanical stirrer, thermowell, stopper, and 2-Liter addition funnel. The aldehyde was diluted with 10 L reagent alcohol and chilled to −13.7° C. Silver nitrate (1226 g, 7.2 mol, 1.5 equivalents) was dissolved in 1800 ml water and added in portions to the aldehyde solution. Addition was complete in 12 minutes while the temperature ranged from −13.7 to −0.9° C. The reaction mixture was cooled to −11.6° C. before adding sodium hydroxide (575 g, 14.4 mol) in 10 L of water. The addition was completed in four hours while the temperature ranged from −11.6 to −0.2° C. The mixture was stirred another hour at −3° C. until GC analysis indicated no further increase in product formation. The reaction mixture was filtered to remove the silver residue and the resulting clear, nearly colorless filtrate was acidified with 1400 ml concentrated hydrochloric acid to pH 1. The mixture was extracted with 3×4000 ml dichloromethane. The combined extracts were washed with 2 gallons brine and then 2×1 gallon brine until the wash pH=5. The extracts were rotary evaporated to 690 g of an oil. This was dissolved in 2000 ml dichloromethane and then extracted with 2 Liters 8% aqueous sodium hydroxide. The aqueous sodium hydroxide extract was washed with 4×600 ml dichloromethane until GC analysis showed no exo-NBMeOH byproduct in the last wash.

The aqueous sodium hydroxide extract was acidified with 310 ml concentrated hydrochloric acid. The resulting phases were separated. The upper aqueous phase was extracted with 2×600 ml dichloromethane. The organic phases were combined and washed with 1000 ml brine. This resulted in a slow-separating milky emulsion. An additional 500 ml dichloromethane and 500 ml water were added to break the emulsion and affect phase separation. The organic portions were dried over sodium sulfate, filtered, and rotary evaporated to 533.8 g, showing 100% purity by GC. NMR analysis in deuteriomethanol solvent shows only 1.3% endo-isomer.

The final brine wash was acidified with 50 ml concentrated hydrochloric acid to pH 1. This was extracted with 3×600 ml dichloromethane. The extracts were washed with 500 ml brine to pH 5, then dried over sodium sulfate, filtered, and rotary evaporated to give 50.4 g, 100% purity exo-NBCO$_2$H by GC. Total yield was 584.4 g (~88% yield, 72% yield from NBCN). NMR analysis indicated the isolated product still contained 6-7% dichloromethane. GC retention time: 5.50 minutes.

Preparation of endo-NBCO$_2$H (via AgNO$_3$ and NaOH)

Endo-NBCHO (948 g of 56.7 wt % in toluene, ~4.4 mol) was placed in a 50-Liter glass flask fitted with mechanical stirrer, thermowell, stopper, and 2-Liter addition funnel. The aldehyde was diluted with 9200 ml reagent alcohol and chilled to −11.4° C. Silver nitrate (1128 g, 6.6 mol, 1.5 equivalents) was dissolved in 1700 ml water and added in portions to the aldehyde solution. Addition was complete in 19 minutes while the temperature ranged from −11.4 to −0.5° C. The reaction mixture was cooled to −8.0° C. before adding sodium hydroxide (529 g, 13.2 mol) in 9.2 Liters of water. The addition was completed in 5 hours 54 minutes while the temperature ranged from −8.0 to −0.2° C. The mixture was stirred another 1.5 hours at <0° C. until GC analysis indicated no further increase in product formation. The reaction mixture was filtered to remove the silver residue, the silver residue washed with reagent alcohol, and the resulting clear, nearly colorless filtrate was acidified with 1200 ml concentrated hydrochloric acid to pH 1. The mixture was extracted with 3×4000 ml dichloromethane. The combined extracts were washed with 3×2 gallons brine until the wash pH=5. The extracts were rotary evaporated to yield 738 g of an oil. This was dissolved in 2000 ml dichloromethane and then extracted with 2 Liters 8% aqueous sodium hydroxide. The aqueous sodium hydroxide extract was washed with 4×1000 ml dichloromethane until GC analysis showed no endo-NB-MeOH byproduct in the last wash.

The aqueous sodium hydroxide extract was acidified with 335 ml concentrated hydrochloric acid to pH 2. The resulting phases were separated. The upper aqueous phase was extracted with 2×500 ml dichloromethane. The organic phases were combined and washed with 1000 ml brine to pH 4. The organic portions were dried over sodium sulfate, filtered, and rotary evaporated to 579.3 g (95% yield, 71% yield from endo-NBCN), showing 99.8% purity endo-NBCO$_2$H by GC. The material crystallized overnight, losing significant mass by evaporation of residual dichloromethane. NMR analysis reveals <5.6% exo-isomer and 1.8 wt % dichloromethane. Final yield was 478.1 g (78.7% yield from endo-NBCHO, 51% yield from endo-NBCN). GC retention time: 5.46 minutes, endo-NBCO$_2$H.

A dichloromethane extract of an aliquot from the initial brine wash revealed via NMR analysis that potentially up to 34 g of ethyl ester may have be present.

Preparation of Exo NBCO$_2$H (via NaClO$_2$)

Exo-NBCHO (87.5:12.5 exo:endo, 1.2 g, 0.01 mol) was dissolved in 50 ml melted t-BuOH. 2-Methyl-2-butene (22 ml, 0.2 mol) was added to the aldehyde solution. NaClO$_2$ (80%, 1.7 g, 0.02 mol) was dissolved in 10 ml deionized water. Sodium dihydrogen phosphate (3.00 g, 0.03 mol) was added to the NaClO$_2$ solution and then sonicated to dissolve, giving an aqueous solution with pH between 4-5. The aldehyde solution was cooled to 17.5° C. before adding the oxidant solution dropwise. The reaction solution became intensely yellow while cooling to 11.1° C. Addition was complete in 8 minutes. GC analysis showed little aldehyde remaining, while the acid product gave an exo/endo ratio of 92:8. The reaction became colorless after stirring 66 minutes at 17.9° C. GC analysis showed no further increase in product formation as the % acid maximized at 89%. The solvents were removed by rotary evaporation and the residue taken up in 10 ml deionized water. The solution was made basic to pH 11 with 12.5 ml 8% aqueous NaOH. This was washed with 2×20 ml dichloromethane and then re-acidified to pH 3 with 7.5 ml 3.5N aqueous HCl. The acidified solution was extracted with 3×20 ml dichloromethane. The dichloromethane extracts were washed with 25 ml brine to pH 5, then dried over sodium sulfate, filtered, and rotary evaporated to give 0.74 g colorless liquid (54% yield). GC analysis shows 97.7% purity with exo/endo ratio of 90:10. NMR analysis indicates 10-15% endo-isomer present, but shows "noise" in the aliphatic region between 2-3.2 ppm. GC retention times: 5.08 min (exo-NBCO$_2$H), 5.15 min (endo-NBCO$_2$H).

Preparation of Endo NBCO$_2$H (via Oxone®)

A 250 mL round bottom, 3-necked flask was equipped with a magnetic stir bar, condenser, stopper, and septum. To the flask was added endo-NBCN (5.96 g, 50 mmol), and the contents were cooled to 0 to 5° C. via an ice-bath. In a continuously purged nitrogen environment, 1.0 M DIBAL-H in hexanes (50 mL, 50 mmols) was added dropwise while stirring. After the addition was complete, the reaction was allowed to stir for 15 minutes at 0 to 5° C. The contents were transferred to a separatory funnel containing cold, dilute HCl (1N, 100 mL). The resulting aldehyde was extracted with cold diethyl ether (4×100 mL) and charged to a flask containing a slurry of DMF (73 mL) and solid, oxidizing agent Oxone® (DuPont CAS-RN 70693-62-8) (2KHSO$_5$.KHSO$_4$.K$_2$SO$_4$) (30.6 g). The mixture was stirred at 0 to 5° C. In an open atmosphere where the aldehyde was oxidized to the corresponding carboxylic acid. The contents were transferred to a separatory funnel where dilute HCl was added to dissolve any residual Oxone®. The aqueous layer was discarded and the organic layer was washed with water (4×100 mL) to remove DMF. The organic layer was extracted with aqueous potassium carbonate (25 wt %), and the aqueous layer was acidified with concentrated HCl. The resulting precipitate was extracted with diethyl ether (3×100 mL), dried over MgSO$_4$, and filtered. The diethyl ether was removed under reduced pressure to afford pure endo-NBCO$_2$H (5.81 g, 84.1%).

Preparation of Exo-Norbornenemethoxymethyl hexafluoropropanol (Exo-NBMMHFP)

NaH (60%, 175.6 g, 4.39 mol) was placed in 4-neck 12-L flask fitted with mechanical stirrer, addition funnel, nitrogen gas inlet, and thermowell. The reaction apparatus had been dried earlier by heating with a hot air drier to 120° C. under a nitrogen flush. Dry THF (1700 ml) was added and the resulting slurry mechanically stirred while cooling to −11.2° C. Exo-NBCH$_2$OH (448 g, 3.61 mol, fractions 4 & 5) was dissolved in 420 ml dry THF and added dropwise to the NaH/THF mixture. Addition time was 25 minutes with the temperature ranging from −12.2° C. to −8.9° C. The reaction was allowed to warm to room temperature (17° C.) and stir overnight. The reaction was cooled to −18.2° C. and 657.2 g (3.65 mol) hexafluoroisobutylene epoxide (HFIBO) was added dropwise. Addition time was 2 hrs with the temperature ranging from −18.4° C. to −0.1° C. GC analysis showed 20.8% unreacted starting material. The mixture was allowed to warm to room temperature (18.7-27.7° C.) and stir another five hours. GC analysis detected no unreacted starting material. The mixture was cooled to −11.3° C. and 1750 ml water was added to quench. The quench time was 81 minutes and quenching temperature reached a maximum of −2.0° C. Then, 375 ml concentrated hydrochloric acid was added, bringing the pH to 2. The deep yellow THF layer was separated from the lower aqueous phase. The aqueous phase was extracted with 2×500 ml MTBE. The organic portions were combined and then split into two 2-L portions. Each was washed with 2×1000 ml brine to pH 5.

The 2nd organic portion gave an emulsion so was diluted further with 3×250 ml MTBE to hasten separation. The combined organic portions were dried over sodium sulfate overnight, filtered, and rotary evaporated to give 1279.8 g of an amber liquid. GC analysis indicated 98.6% purity. The crude product was vacuum distilled through a 12-inch Vigreux column:

1. 22.50° C. (1.65 Torr)-91.80° C. (1.15 Torr), 33.38 g, 95.3% (GC), contains THF
2. 89.20° C. (0.98 Torr)-76.20° C. (0.89 Torr), 121.08 g, 98.3% (GC), NMR ok
3. 75.0° C. (0.84 Torr)-64.9° C. (1.00 Torr), 257.99 g, 98.8% (GC), NMR ok
4. 64.4° C. (0.86 Torr)-62.2° C. (0.95 Torr), 637.58 g, 99.7% (GC), NMR ok
5. 61.4° C. (0.91 Torr)-63.0° C. (0.94 Torr), 19.32 g, 98.1% (GC), extra signals in NMR
6. 53.8° C. (0.91 Torr)-124.1° C. (0.98 Torr), 4.63 g, yellow
7. 120.2-140.1° C. (0.96 Torr), 5.70 g, yellow Pot, 63.5 g Fractions 2, 3, and 4 were combined to give 1016.65 g (93% yield) with 99.2% (GC) purity. Retention time: 4.902 min.

Preparation of Endo-NBMMHFP

NaH (60%, 17.73 g, 0.44 mol) was placed in 500-ml flask fitted with mechanical stirrer, addition funnel, nitrogen gas inlet, and thermowell. The reaction apparatus had been dried earlier with a hot air drier to ~120° C. under a nitrogen flush. Dry THF (200 ml) was added and the resulting slurry mechanically stirred while cooling to −16.8° C. Endo-NBCH$_2$OH (50.0 g, 0.403 mol) was dissolved in 50 ml dry THF and added dropwise to the NaH/THF mixture. Addition time was 32 minutes with the temperature ranging from −16.8° C. to −0.8° C. The white slurry was allowed to warm to room temperature and stir overnight. The reaction was cooled to −17.4° C. and 72.8 g (0.40 mol) hexafluoroisobutylene epoxide (HFIBO) was added dropwise. Addition time was 26 min with the temperature ranging from −15.1° C. to −2.4° C. The cooling bath was removed and the reaction very quickly warmed to 11.3° C., where it was cooled briefly again to slow the exotherm. The reaction was stirred 4.5 hours at 15-18° C. until GC analysis showed no further change. The mixture was cooled to −8° C. and 200 ml water was added to quench. The quenching temperature reached a maximum of +0.2° C. Then, 40 ml of concentrated hydrochloric acid was added. The golden THF layer was separated from the lower aqueous phase. The aqueous phase was extracted with 2×100 ml MTBE. The organic portions were combined and washed with 3×100 ml brine, then 4×200 ml brine to pH 6. The extracts were dried over sodium sulfate, filtered, and rotary evaporated to give 129.06 g of an oil. GC analysis indicated 93.9% purity and 4.4% unreacted endo-alcohol. The material was distilled in the Kugelrohr oven, giving 87.03 g at 110° C. (2 torr) with 98.5% purity and 1.5% endo-NBMeOH. An additional 1.67 g was collected at 120-130° C. (2 torr) with 98.9% purity and 1.1% endo-NBMeOH. The 87-g sample was redistilled in the Kugelrohr oven to give 50.80 g at 104° C. (1 torr) with 99.2% purity and contained 0.8% endo-NBMeOH. A forerun of 28.18 g was also collected at 104° C. (1 torr), giving 96.6% purity and 3.4% endo-NBMeOH. Yield of >99% purity product was 41%. Yield of adduct with >98% purity was 72%. GC retention times were 5.29 minutes (endo-NBMMHFP), 3.13 min (endo-NBMeOH).

Exo-Norbornenylmethoxydiphenylmethylsilane (Exo-NBCH$_2$OSiMePh$_2$)

A charge of exo-norbornenyl methanol (96 grams, 0.77 mol) was added in a five-necked, 500 mL glass jacketed reactor, which was sparged with nitrogen. The reactor was heated via a heating/cooling circulating water bath with a 75° C. set point. At an internal reactor temperature of 75° C., diphenylmethyl(dimethylamino silane (171 grams, 0.71 mol) was added drop wise through an addition funnel to prevent an exothermic reaction from occurring. Next, the internal reactor temperature was heated to 100° C. It was held for up to 24 hours and sampled with GC monitoring to ensure the dimethylamine content was less than 1% in the reactor. The reactor was connected to an acid base scrubber, which neutralized the dimethylamine. The reaction mixture was cooled and collected into a bottle. The crude material of exo-norbornenylmethoxydiphenylmethylsilane (209 grams, 71% yield) was purified through a short path head distillation setup at 150° C. and 60 mTorr to yield 140 grams (>98%, 100% exo content) as a colorless liquids. Proton NMR indicated only the presence of exo-NBCH$_2$OSiMePH$_2$, indicating that the diastereomeric purity of the starting material was maintained.

Exo-Norbornenyl Ethoxy Diphenylmethyl Silane
(Exo-NBCH$_2$CH$_2$OSiMePh$_2$)

A charge of exo-norbornenylethanol (exo-NBCH$_2$CH$_2$OH) (246 grams, 1.78 mol) was added in a five-necked, 500 mL glass jacketed reactor, which was sparged with nitrogen. The reactor was heated via a heating/cooling circulating water bath with a 75° C. set point. At an internal reactor temperature of 75° C., diphenylmethyl (dimethylamino)silane (390 grams, 1.62 mol) was added drop wise through an addition funnel to prevent an exothermic reaction from occurring. Next, the internal reactor temperature was heated to 100° C. It was held for 24 hours and sampled with GC monitoring to ensure all the dimethylamine gas was less than 1% in the reactor. The reactor was connected to an acid base scrubber, which neutralized the dimethylamine being evolved. The reaction mixture was cooled and collected into a bottle. The crude material of exo-norbornenylethoxydiphenylmethylsilane (540 grams, 78% yield) was purified through a short path head distillation setup at 160° C. and 50 mTorr to yield 317 grams (>98% purity) as a colorless liquid. Proton NMR indicated exo-NBCH$_2$CH$_2$OSiMePh$_2$ product possessed the same diastereomeric purity as the starting exo-NBCH$_2$CH$_2$OH.

Synthesis of endo-Norbornene-carboxylic acid tetrahydro-2-oxo-3-furanyl ester (endo-GBLNB)

An appropriately sized flask was charged with α-Br-δ-butyolactone (26.1 g, 158 mmols). After equipping the flask with a thermometer, septum, and condenser, endo-NBCO$_2$H (20.0 g, 145 mmols) and tetrahydrofuran (100 mL) was added. Under a nitrogen sweep, the solution was cooled to ~5° C. with the aid of an ice-bath. Next, triethylamine (19.1 g, 189 mmols) was injected through the septum and the contents were allowed to warm to ambient temperature after which reflux for 20 h. After allowing to cool to ambient temperature, the contents were filtered to separate byproduct. To the filtrate was diluted with methylene chloride, and the solution was extracted with 5% sodium bicarbonate (2×50 mL) and water (1×50 mL). The solution was dried over magnesium sulfate and filtered. Diethyl ether was added to the solution to aid in recrystallization. Endo-GBLNB was collected by filtration (21.5 g, 67% yield). Proton NMR indicated endo-GBLNB product possessed the same diastereomeric purity as the starting endo-NBCO$_2$H.

Synthesis of exo-GBLNB

An appropriately sized flask was charged with α-Br-δ-butyolactone (26.3 g, 160 mmols). After equipping the flask with a thermometer, septum, and condenser, endo-NBCO2H (20.0 g, 145 mmols) and tetrahydrofuran (100 mL) was added. Under a nitrogen sweep, the solution was cooled to ~5° C. with the aid of an ice-bath. Next, triethylamine (19.1 g, 189 mmols) was injected through the septum and the contents were allowed to warm to ambient temperature after which reflux for 20 h. After allowing to cool to ambient temperature, the contents were filtered to separate byproduct. To the filtrate was diluted with methylene chloride, and the solution was extracted with 5% sodium bicarbonate (2×50 mL) and water (1×50 mL). The solution was dried over magnesium sulfate and filtered. Diethyl ether was added to the solution to aid in recrystallization. Exo-GBLNB was collected by filtration. Proton NMR indicated exo-GBLNB product possessed the same diastereomeric purity as the starting exo-NBCO$_2$H.

Synthesis of endo-Norbornene-carboxylic acid ethylcyclohexyl ester (endo-ECHENB)

Triethylamine (5.54 g, 54.8 mmols) and p-toluene sulfonyl chloride (8.35 g, 43.8 mmols) were dissolved in dimethylacetamide (2.29 g) in a sealed septum bottle. The solution was injected into an appropriately sized bottle containing endo-NBCO$_2$H (5.04 g, 36.5 mmols), 1-ethylcyclohexanol (5.62 g, 43.8 mmols), and dimethylacetamide (2.00 g) heated to 50° C. under nitrogen. After heating for 20 h, the solution was precipitated into tetrahydrofuran and filtered to remove triethylamine hydrogen chloride. Toluene was added to the filtrate, and it was washed with 15% sodium hydroxide (2×30 mL), and water (2×50 mL). Purification via column chromatography afforded endo-ECHENB. Proton NMR indicated the product to be high purity endo-ECHENB.

Synthesis of exo-ECHENB

Triethylamine (5.54 g, 54.7 mmols) and p-toluene sulfonyl chloride (8.35 g, 43.8 mmols) were dissolved in dimethylacetamide (2.29 g) in a sealed septum bottle. The solution was injected into an appropriately sized bottle containing exo-NBCO2H (5.04 g, 36.5 mmols), 1-ethylcyclohexanol (5.62 g, 43.8 mmols), and dimethylacetamide (2.00 g) heated to 50° C. under nitrogen. After heating for 20 h, the solution was precipitated into tetrahydrofuran and filtered to remove triethylamine hydrogen chloride. Toluene was added to the filtrate, and it was washed with 15% sodium hydroxide (2×30 mL), and water (2×50 mL). Purification via column chromatography afforded exo-ECHENB. Proton NMR indicated the product to be high purity endo-ECHENB.

Synthesis of exo-/endo-TMSETD (tetracyclododecenyl-ethyltrimethoxysilane) from exo-/endo-TMSENB A high-pressure microtube was charged with TMSENB (2.74 g, 11.3 mmols) and DCPD (0.26 g, 2.0 mmols). The microtube was heated to 220° C. for 4 h, and the contents were analyzed. GC retention times: 9.740 (TMSENB, 69.3 area %), 10.973 (trimers, 1.58 area %), 14.919 (TMSETD, 16.8 area %), 15.466 (TMSETD, 8.4 area %). Total TMSETD yield was 25.2% from GC area %.

Synthesis of exo-/endo-TMSETD from exo-TMSENB

A high-pressure microtube was charged with exo-TMSENB (2.74 g, 11.3 mmols) and DCPD (0.26 g, 2.0 mmols). The microtube was heated to 220° C. for 4 h, and the contents were analyzed. GC retention times: 9.763 (TMSENB, 54.9 area %), 10.974 (trimers, 1.52 area %), 14.808 (TMSETD, 2.03 area %), 15.625 (TMSETD, 38.4 area %). Total TMSETD yield was 40.43% from GC area %.

Synthesis of exo-/endo-TDCN (octahydrodimethanonaphthalenecarbonitrile) from exo-NBCN A high-pressure microtube was charged with exo-NBCN (1.76 g, 14.8 mmols) and CPD (0.49 g, 7.4 mmols). The microtube was heated to 220° C. for 4 h, and the contents were analyzed. GC retention times: 12.716 (TDCN, 5.7 area %), 13.005 (TDCN, 1.1 area %), 13.386 (TDCN, 46.8 area %).

Polymerization Example

Preparation of HFANB/MeOAcNB

Three polymerizations were performed. For each, a diastereomeric mixture of HFANB (0.017 mmol) was charged to an appropriately sized reaction vessel with 0.014 mmol of either essentially pure endo-NBMeOAc (polymerization A), a diastereomeric mixture of NBMeOAc (polymerization B), or essentially pure exo-NBMeOAc (polymerization C). In addition to the aforementioned monomers, the reaction vessels were each charged with N-dimethylanilinium tetrakis (pentafluorophenyl) borate (DANFABA 0.090 mmol), ethyl acetate (2.5 g) and toluene (7.4 g). Then (acac)palladium(II) bis(acetonitrile)tetrakis(pentafluorophenyl)borate] (Pd-967 0.03 mmol) was added to each reaction vessel followed by the addition of 3.26 mmol of formic acid. Each reaction vessel was heated to 90° C. and stirred for 18 hours. After cooling, a total solids analysis was done to determine percent conversion (using a total solids analyzer (Mettler Toledo HR73 halogen moisture analyzer) and a GPC analysis was used to determine molecular weight (gel permeation chromatography using poly(styrene) standards). Next, each polymer was purified to remove residual catalyst and then precipitated into hexane and dried in a vacuum oven.

TABLE 2

| Example | Isomer | Formic Acid (mol % on monomer) | % Conv. | Mw | Mw/Mn |
|---|---|---|---|---|---|
| A | endo/exo-HFA; endo-MeOAcNB | 10 | 97 | 2373 | 1.34 |
| B | endo/exo-HFA; endo/exo-MeOAcNB | 10 | 100 | 2634 | 1.40 |
| C | endo/exo-HFA; exo-MeOAcNB | 10 | 100 | 3387 | 1.49 |

As seen in Table 2, the essentially pure exo- and endo-NBMeOAc monomers are effectively polymerized. Further, it can be seen that polymerization Example A results in the lowest molecular weight and % conversion while polymerization Example C has the highest molecular weight and polymerization Example B exhibits an intermediate molecular weight. Thus, such polymerization examples demonstrate the higher reactivity of the exo-NBMeOAc as compared to both the diastereomeric mixture and the endo-epimer. Still further, it should be apparent that having essentially pure exo- and endo-isomers allows for polymerization embodiments in accordance with the present invention to be directed to making alternating polymers, block polymers and gradient polymers where the specific configurations of such polymers are based on the isomeric configuration of the specific repeating units employed as well as different materials.

By now it should be realized that by and through the above examples, data and discussion, embodiments in accordance with the present invention have been demonstrated. For example, embodiments that provide for the preparation of both endo- and exo-epimers of a 5-NBCHO have been shown as well as embodiments that demonstrate the forming of both endo- and exo-epimers of a variety of other norbornene-type monomers derived from such 5-NBCHO isomers. Further, it has been taught that bis-cyano [bis-carboxaldehyde]norbornenes and TD or higher homologs of such carboxaldehydes can also be used to form a wide variety of desireable norbornene-type monomers. Still further it has been taught that a variety of homologation reactions can be employed to increase the length of functional groups by inserting one or more methylene groups therein.

Additionally, embodiments in accordance with the present invention that are directed to the polymerization of essentially pure monomeric epimers have been described and shown. Also described are embodiments of the present invention that are directed to polymerization of norbornene-type monomers where the monomer feedstock for the polymerization encompasses a specific ratio of endo- and exo-epimers of one or several monomer types. As it will be understood, only by and through embodiments of the present invention directed to preparing both the endo- and exo-epimer of a variety of monomer types is it possible to determine a desired ratio of such epimers for any one (or several) monomer-type(s) and then create a monomer feedstock having this (these) desired ratio(s) and to polymerize such a feedstock to create a polymer that incorporates such epimers as repeating units. Still further, it will be appreciated that such polymers having such desired ratios are then tailored to have specific polymer properties. For example a desired dissolution rate in an alkali solution, molecular weight or a specific elongation to break or the like. For example as shown in Table 2, where an HFANB/NBMeOAc polymer having a Mw of about 2400 is desired, such can be obtained by using an essentially pure endo-isomer of NBMeOAc while where a Mw of about 3400 is needed, using the corresponding essentially pure exo-isomer would be appropriate.

It should be appreciated that the synthetic yields of the TD monomers made from high purity exo-norbornene analogs, shown above, are indicative of the higher reactivity of such monomers when compared to an analogous endo-monomer or a diastereomeric mixture of such monomers. Thus the total yield of TMSETD made from exo-/endo-TMSENB is only about 60% of the yield obtained when the starting material was essentially pure exo-TMSENB. Still further, it should be appreciated that in comparing the reactions of analogous exo- and endo-isomers, the exo-isomer generally exhibits higher reactivity and transformations of such an exo-isomer results in shorter reaction times and higher yields than the endo-isomer.

While the invention has been explained in relation to descriptions of various embodiments and examples, it is to be understood that modifications thereof will become apparent to those skilled in the art upon reading this specification. Any such modifications are therefore within the scope and spirit of the embodiments of the present invention and shall be understood to fall within the scope of the appended claims.

What is claimed is:

1. A method for forming an essentially pure exo- and/or endo-substituted norbornene monomers, comprising:
   forming a diastereomeric mixture of norbornenecarbonitrile (NBCN) via a Diels-Alder reaction;
   separating the exo- and endo-diastereomers of such diastereomeric mixture;
   first converting an individual NBCN diastereomer to the analogous diastereomeric norbornenecarboxaldehyde (NBCHO); and
   second converting an individual NBCHO diastereomer to one of the analogous norbornenecarboxylic acid or alcohol.

2. The method of claim 1, where the first converting comprises charging a reaction vessel with a metal hydride and an individual NBCN diastereomer to effect a reduction of said NBCN, and subsequently hydrolysing the reaction intermediate.

3. The method of claim 1, where the second converting comprises charging a reaction vessel with a hydride donor reagent and an individual NBCHO diastereomer to effect a reduction of said NBCHO.

4. The method of claim 1, where the second converting comprises charging a reaction vessel with an appropriate oxidizing agent and an individual NBCHO diastereomer to effect an oxidation of said NBCHO.

5. The method of claim 2, where the second converting comprises charging a reaction vessel with an appropriate oxidizing agent and an individual NBCHO diastereomer to effect an oxidation of said NBCHO.

6. The method of claim 2, where the second converting comprises charging a reaction vessel with an appropriate reducing agent and an individual NBCHO diastereomer to effect a reduction of said NBCHO.

7. The method of claim 2, where the second converting comprises charging a reaction vessel with a hydride donor reagent and an individual NBCHO diastereomer to effect a reduction of said NBCHO.

8. The method of claim 2, where the metal hydride comprises lithium aluminum hydride, alkyl aluminum hydrides, alkoxyaluminum hydrides, or dialkylamino lithium hydrides.

9. The method of claim 1, further comprising
   using the analogous norbornenecarboxylic acid or alcohol in a transition metal polymerization.

10. The method of claim 1, where separating the exo- and endo-diastereomers of the diastereomeric mixture comprises distilling the exo- and endo-diastereomers.

11. The method of claim 1, where separating the exo- and endo-diastereomers of the diastereomeric mixture comprises fractionally distilling the exo- and endo-diastereomers.

12. The method of claim 1, where the diastereomeric mixture of NBCN comprises bis-norbornenecarbonitriles.

13. A method for forming at least a 95% diastereomerically pure exo- and/or endo-substituted norbornene monomers, comprising:
   forming a diastereomeric mixture of norbornenecarbonitrile (NBCN) via a Diels-Alder reaction separating the exo- and endo-diastereomers of such diastereomeric mixture;
   first converting an individual NBCN diastereomer to the analogous diastereomeric norbornenecarboxaldehyde (NBCHO); and
   second converting an individual NBCHO diastereomer to one of the analogous norbornenecarboxylic acid or alcohol.

14. The method of claim 13, where the first converting comprises charging a reaction vessel with a metal hydride and an individual NBCN diastereomer to effect a reduction of said NBCN, and subsequently hydrolysing the reaction intermediate.

15. The method of claim 13, where the second converting comprises charging a reaction vessel with a hydride donor reagent and an individual NBCHO diastereomer to effect a reduction of said NBCHO.

16. The method of claim 13, where the second converting comprises charging a reaction vessel with an appropriate oxidizing agent and an individual NBCHO diastereomer to effect an oxidation of said NBCHO.

17. The method of claim 14, where the metal hydride comprises lithium aluminum hydride, alkyl aluminum hydrides, alkoxyaluminum hydrides, or dialkylamino lithium hydrides.

18. The method of claim 13, further comprising using the analogous norbornenecarboxylic acid or alcohol in a transition metal polymerization.

19. A method for forming an essentially pure exo- and/or endo-substituted norbornene monomers, comprising:
   forming a diastereomeric mixture of 5-norbornenecarbonitrile (5-NBCN) via a Diels-Alder reaction;
   separating the exo- and endo-diastereomers of such diastereomeric mixture;
   first converting an individual 5-NBCN diastereomer to the analogous diastereomeric norbornenecarboxaldehyde (NBCHO); and
   second converting an individual NBCHO diastereomer to one of the analogous norbornenecarboxylic acid or alcohol.

20. The method of claim 1, where the first converting comprises charging a reaction vessel with a metal hydride and an individual 5-NBCN diastereomer to effect a reduction of said 5-NBCN, and subsequently hydrolysing the reaction intermediate.

* * * * *